(12) United States Patent
Shi et al.

(10) Patent No.: US 11,666,241 B2
(45) Date of Patent: Jun. 6, 2023

(54) SYSTEM AND METHOD FOR MEDICAL IMAGING

(71) Applicant: SHANGHAI UNITED IMAGING HEALTHCARE CO., LTD., Shanghai (CN)

(72) Inventors: Yuhang Shi, Shanghai (CN); Zheng Zhang, Shanghai (CN); Tingrong Shi, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 636 days.

(21) Appl. No.: 16/726,868

(22) Filed: Dec. 25, 2019

(65) Prior Publication Data

US 2020/0245894 A1    Aug. 6, 2020

(30) Foreign Application Priority Data

Feb. 2, 2019  (CN) .......................... 201910107788.9
Apr. 22, 2019  (CN) .......................... 201910323509.2

(51) Int. Cl.
*A61B 5/055* (2006.01)
*A61B 6/00* (2006.01)
*A61B 8/00* (2006.01)

(52) U.S. Cl.
CPC .............. *A61B 5/055* (2013.01); *A61B 6/488* (2013.01); *A61B 6/54* (2013.01); *A61B 8/40* (2013.01); *A61B 8/54* (2013.01)

(58) Field of Classification Search
CPC ....... A61B 5/055; A61B 5/0037; A61B 6/488; A61B 6/54; A61B 6/04; A61B 8/40; A61B 8/54; A61B 8/00
See application file for complete search history.

(56) References Cited

U.S. PATENT DOCUMENTS 5,329,567 A * 7/1994 Ikebe .................. A61B 6/4476
                                                    378/65
2015/0003577 A1    1/2015 Aulbach et al.

FOREIGN PATENT DOCUMENTS

CN       100586368 C    2/2010
CN       104586421 A    5/2015
CN       106388851 A    2/2017

(Continued)

OTHER PUBLICATIONS

First Office Action in Chinese Application No. 201910323509.2 dated Nov. 2, 2022, 16 pages.

*Primary Examiner* — Peter Luong

(74) *Attorney, Agent, or Firm* — Metis IP LLC

(57) ABSTRACT

The present disclosure directs to a system and method for automated positioning of a subject. The method may include obtaining a scout image of a subject when the subject is positioned at a first position in an apparatus. The method may also include determining location information of a reference structure of the subject based on the scout image. The method may also include determining an offset between the first position of the subject relative to a characteristic point of the apparatus according to the location information of the reference structure. The method may further include moving the subject to a second position based on the offset. The method may still further include performing, using the apparatus, a procedure relating to a target structure of the subject located at the second position.

16 Claims, 11 Drawing Sheets

(56) References Cited

FOREIGN PATENT DOCUMENTS

| CN | 106943678 A | 7/2017 |
|---|---|---|
| CN | 106963380 A | 7/2017 |
| CN | 107403287 A | 11/2017 |
| CN | 107789001 A | 3/2018 |
| CN | 109009202 A | 12/2018 |
| CN | 109276248 A | 1/2019 |
| CN | 109567843 A | 4/2019 |

* cited by examiner

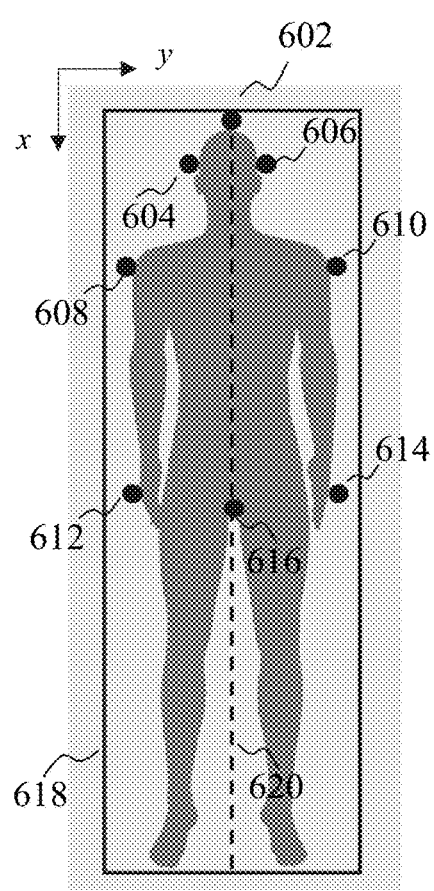
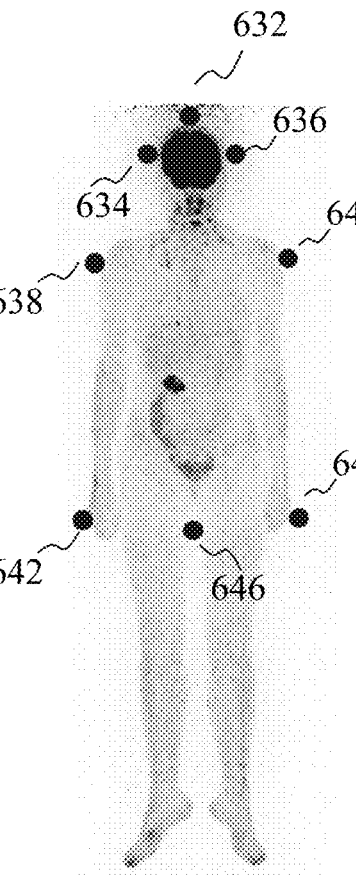
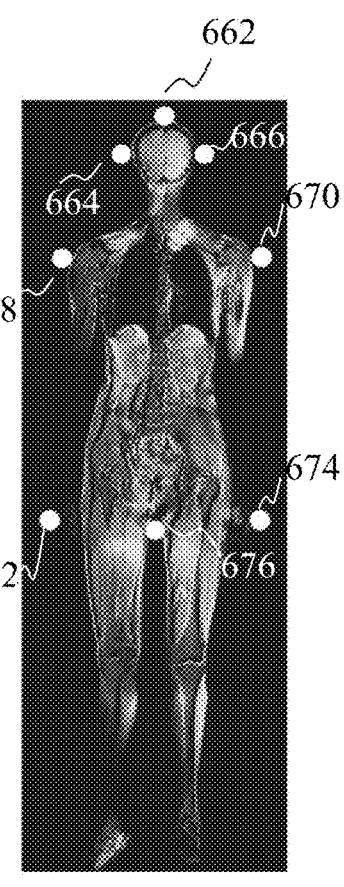
FIG. 6(a)  FIG. 6(b)  FIG. 6(c)

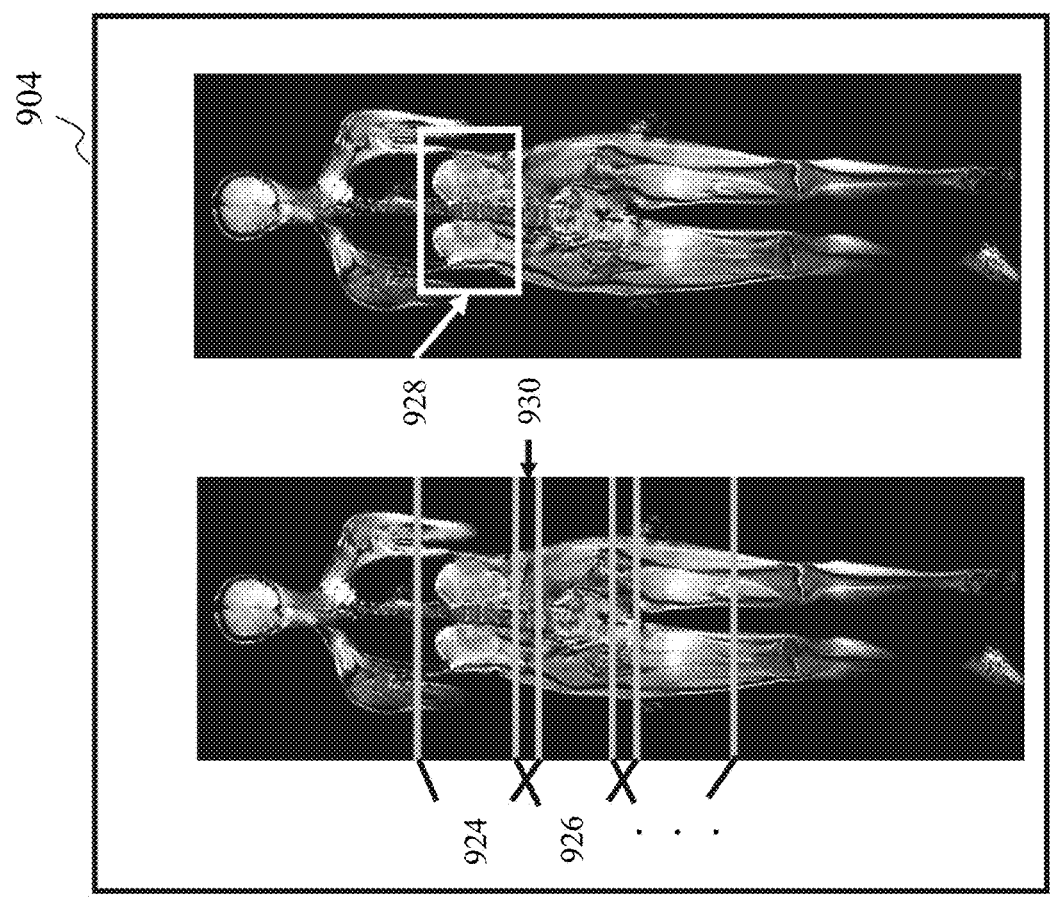
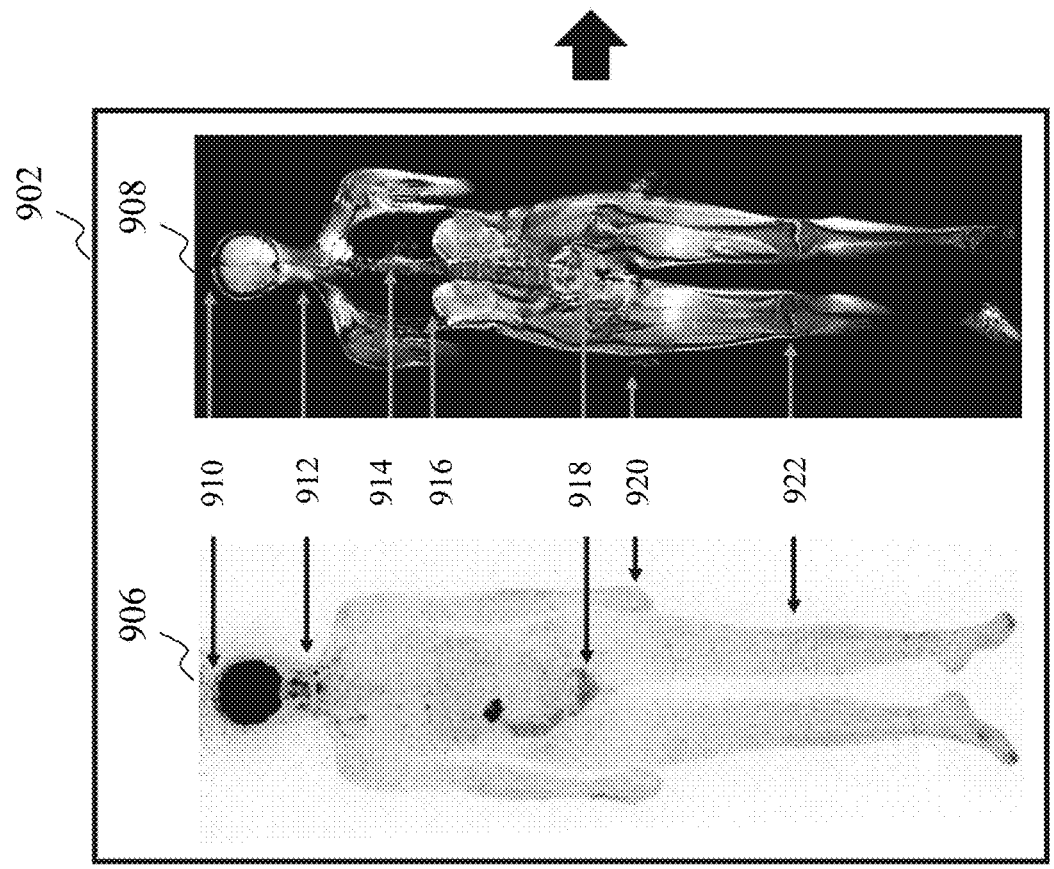
FIG. 9

SYSTEM AND METHOD FOR MEDICAL IMAGING

CROSS-REFERENCE TO RELATED APPLICATIONS

This application claims priority to Chinese Application No. 201910107788.9, filed on Feb. 2, 2019, and Chinese Application No. 201910323509.2, filed on Apr. 22, 2019, the contents of which are hereby incorporated by reference.

TECHNICAL FIELD

The present disclosure generally relates to systems and methods for medical imaging, and more particularly, to systems and methods for automated positioning of a subject for medical imaging and/or treatment.

BACKGROUND

Medical imaging or treatment systems including, e.g., a X-ray imaging system, a positron emission tomography (PET) system, a magnetic resonance (MR) system, a computed tomography (CT) system, a single-photon emission computed tomography (SPECT) system, an ultrasound system, a radioisotope imaging system, a radiotherapy system, etc., are widely used in clinical diagnosis and/or treatment of various of diseases. A medical imaging system may scan one or more target structures of a subject and generate a medical image. A treatment system may deliver a treatment, e.g., treatment by radiation, to one or more target structures of a subject. Exemplary target structures of a subject may include a bone, muscle, a blood vessel, an organ, etc., or a combination thereof, of the subject.

In an aspect, in order to obtain an image with better quality and/or perform a treatment with better efficacy, the position of a subject, or a portion thereof, e.g., a target structure of the subject, needs to satisfy a condition during a scanning process. Conventionally, a scan to facilitate the positioning is performed to provide a scout image before an imaging scan so as to obtain an image indicating a location of a subject, or a portion thereof. Then a doctor analyzes and adjusts the location of the subject, or a portion thereof, e.g., a target structure of the subject, based on the scout image. The analysis by the doctor is subjective, and may depend on the experience of the doctor, thus affecting the quality of medical images acquired based on the patient positioning, the accuracy of the diagnosis performed based on such medical images, and/or the efficacy of a treatment performed based on such medical images or the subject positioning.

In another aspect, as for signal acquisition of the whole body or a part of the body of the subject, multiple scanning regions corresponding to different bed positions may be needed due to the limitations including, e.g., the length of the detector in a longitudinal direction. Data acquired from the multiple scanning regions may be reconstructed to provide multiple sub-images, which may be spliced into an image of the whole body or a portion thereof. In order to improve the scanning time and the quality of such an image of the whole body (or a portion thereof), different scanning schemes may be used for different scanning regions. At present, a doctor determines a range for signal acquisition of the whole body or a specific part of the body of the subject from a scout image (e.g., a scout image of the whole body obtained from a pre-scan) manually. The doctor also estimates positions of one or more structures of interest (e.g., the liver, the heart, etc., of the subject). Then the doctor determines the number (or count) of scanning regions to be scanned according to the scout image and the estimated positions of the one or more structures of interest. The doctor further adjusts a range of each scanning region, and determines overlapping regions between two adjacent scanning regions manually. An imaging scan is performed on the multiple scanning regions. In general, the dimensions of the overlapping regions are set to a same value. The process may be time-consuming and laborious for the doctor, and the estimated positions of the one or more structures of interest may be inaccurate, thus resulting in an undesired arrangement of the scanning/treatment regions and affecting the imaging quality of the whole body or a specific part of the body of the subject, and/or the efficacy of the treatment. Thus, it is desirable for a system and method for positioning a subject or a portion thereof more accurately and efficiently.

SUMMARY

According to a first aspect of the present disclosure, a system comprising at least one storage device storing a set of instructions, and at least one processor configured to communicate with the at least one storage device may be provided. When executing the set of instructions, the at least one processor is directed to perform operations including obtaining a scout image of a subject when the subject is positioned at a first position in an apparatus; determining location information of a reference structure of the subject based on the scout image; determining an offset between the first position of the subject relative to a characteristic point of the apparatus according to the location information of the reference structure; moving the subject to a second position based on the offset; and performing, using the apparatus, a procedure relating to a target structure of the subject located at the second position.

In some embodiments, determining the offset between the first position of the subject relative to a characteristic point of the apparatus according to the location information of the reference structure may include determining a coordinate of an edge point or a center point of the reference structure at the first position and a coordinate of the characteristic point of the apparatus; and determining the offset between the first position of the subject relative to a characteristic point of the apparatus based on the coordinate of the edge point or the center point of the reference structure at the first position and the coordinate of the characteristic point of the apparatus.

In some embodiments, the apparatus may include an imaging device, wherein the characteristic point of the apparatus includes an imaging center of the imaging device, and performing, using the apparatus, the procedure on the target structure of the subject located at the second position includes directing the imaging device to scan an imaging-scan region including the target structure to obtain image data; and reconstructing an image of the target structure based on the image data.

In some embodiments, the apparatus may include a treatment device, wherein the characteristic point of the apparatus includes an isocenter of the treatment device, and performing, using the apparatus, the procedure on the target structure of the subject located at the second position includes directing the treatment device to deliver a dose of a treatment medium to the target structure.

In some embodiments, obtaining the scout image of the subject positioned at the first position in the apparatus includes generating scanning instructions for scanning the subject or a portion of the subject when the subject is positioned at the first position in the apparatus; determining a pre-scan region based on the scanning instructions; obtaining pre-scan data of the pre-scan region by directing an imaging scanner to scan the pre-scan region; reconstructing one or more sub-images of the pre-scan region based on the pre-scan data; and generating the scout image based on the one or more sub-images.

In some embodiments, the one or more sub-images may include at least one of a magnetic resonance (MR) image, a computed tomography (CT) image, or a positron emission tomography (PET) image.

In some embodiments, the operations may further include determining location information of the target structure according to the scout image; and determining an auxiliary offset of the subject according to the location information of the target structure and an imaging-scan region.

In some embodiments, the target structure may be different from the reference structure.

According to a second aspect of the present disclosure, a system comprising at least one storage device storing a set of instructions, and at least one processor configured to communicate with the at least one storage device may be provided. When executing the set of instructions, the at least one processor is directed to perform operations including obtaining a scout image of a subject; determining location information of at least one target structure of the subject based on the scout image; and determining a protocol for performing a procedure regarding the at least one target structure according to the location information of the at least one target structure of the subject.

In some embodiments, the procedure may include imaging the at least one target structure of the subject or performing a treatment on the at least one target structure of the subject.

In some embodiments, the operations may further include directing an imaging scanner to scan an imaging-scan region including the target structure according to the protocol to obtain image data; and reconstructing an image of the target structure based on the image data.

In some embodiments, obtaining the scout image of the subject may include generating scanning instructions for scanning the subject or a portion thereof; determining a pre-scan region based on the scanning instructions; obtaining pre-scan data of the pre-scan region by directing an imaging scanner to scan the pre-scan region; reconstructing one or more sub-images of the pre-scan region based on the pre-scan data; and generating the scout image based on the one or more sub-images.

In some embodiments, the one or more sub-images may include at least one of one or more magnetic resonance (MR) images, a computed tomography (CT) image, a positron emission tomography (PET) image.

In some embodiments, determining the location information of the at least one target structure of the subject based on the scout image may include determining a coordinate of an edge point or a center point of the target structure in a length direction of the subject in the scout image.

In some embodiments, the protocol may include one or more scanning regions and scanning parameters regarding the one or more scanning regions.

In some embodiments, determining the protocol for performing the procedure regarding the at least one target structure according to the location information of the at least one target structure of the subject may include determining the one or more scanning regions with respect to the at least one target structure based on a coordinate of the target structure.

In some embodiments, the at least one target structure includes a static structure or a dynamic structure.

In some embodiments, the operations may further include determining that at least one of the at least one target structure includes a dynamic structure; determining a coordinate of a center of the dynamic structure; and positioning the dynamic structure in a non-overlapping region in one of two adjacent scanning regions according to the coordinate of the center of the dynamic structure.

In some embodiments, positioning the dynamic structure in the non-overlapping region in one of two adjacent scanning regions according to the coordinate of the center of the dynamic structure may include designating the coordinate of the center of the dynamic structure as a coordinate of the center of the one of the two scanning regions where the dynamic structure is located.

In some embodiments, the operations may further include determining that at least one of the at least one target structure includes a static structure; determining coordinates of an upper edge and a lower edge of the static structure; and positioning the static structure in an overlapping region of two adjacent scanning regions according to the coordinates of the upper edge and the lower edge of the static structure.

According to a third aspect of the present disclosure, a method implemented on a computing apparatus having at least one computer readable storage medium storing a set of instructions and at least one processor executing the set of instructions may be provided. The method may include obtaining a scout image of a subject when the subject is positioned at a first position in an apparatus; determining location information of a reference structure of the subject based on the scout image; determining an offset between the first position of the subject relative to a characteristic point of the apparatus according to the location information of the reference structure; moving the subject to a second position based on the offset; and performing, using the apparatus, a procedure relating to a target structure of the subject located at the second position.

According to a third aspect of the present disclosure, a method implemented on a computing apparatus having at least one computer readable storage medium storing a set of instructions and at least one processor executing the set of instructions may be provided. The method may include obtaining a scout image of a subject; determining location information of at least one target structure of the subject based on the scout image; and determining a protocol for performing a procedure regarding the at least one target structure according to the location information of the at least one target structure of the subject.

According to a fifth aspect of the present disclosure, a non-transitory computer readable medium, comprising at least one set of instructions, wherein when executed by at least one processor of a computing apparatus, the at least one set of instructions causes the computing apparatus to perform a method may be provided. The method may include obtaining a scout image of a subject when the subject is positioned at a first position in an apparatus; determining location information of a reference structure of the subject based on the scout image; determining an offset between the first position of the subject relative to a characteristic point of the apparatus according to the location information of the reference structure; moving the subject to a second position based on the offset; and performing, using the apparatus, a procedure relating to a target structure of the subject located at the second position.

According to a sixth aspect of the present disclosure, a non-transitory computer readable medium, comprising at least one set of instructions, wherein when executed by at least one processor of a computing apparatus, the at least one set of instructions causes the computing apparatus to perform a method may be provided. The method may include obtaining a scout image of a subject; determining location information of at least one target structure of the subject based on the scout image; and determining a protocol for performing a procedure regarding the at least one target structure according to the location information of the at least one target structure of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6(a) includes a schematic diagram of a human body according to some embodiments of the present disclosure;

FIG. 6(b) includes a scout image of the human body generated by scanning the human body using a PET scanner according to some embodiments of the present disclosure;

FIG. 6(c) includes a scout image of the human body generated by scanning the human body using an MR scanner according to some embodiments of the present disclosure;

FIG. 9 is a schematic diagram of an exemplary imaging scan with automated positioning of a subject according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
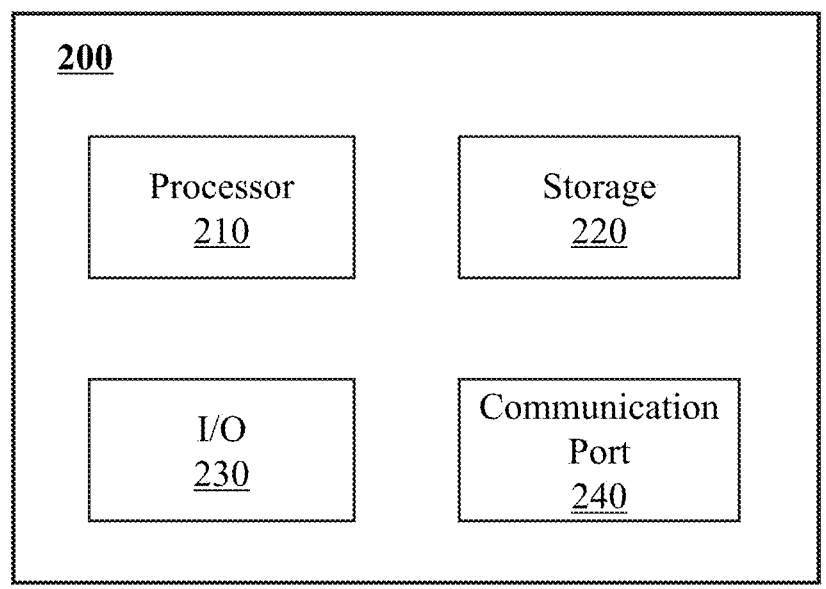
FIG. 2 is a schematic diagram illustrating hardware and/or software components of an exemplary computing apparatus according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on a computing apparatus (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing apparatus, for execution by the computing apparatus. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing apparatus functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive imaging and/or treatment, such as for disease diagnosis, treatment or research purposes. In some embodiments, the system may be a radiation therapy system, a computed tomography (CT) system, an emission computed tomography (ECT) system, an X-ray photography system, a positron emission tomography (PET) system, or the like, or any combination thereof. For illustration purposes, the disclosure describes systems and methods for radiation therapy. The term "image" used in this disclosure may refer to a 2D image, a 3D image, or a 4D image. In some embodiments, the term "image" may refer to an image of a region, e.g., a region of interest (ROI), of a patient. The term "region of interest" or "ROI" used in this disclosure may refer to a part of an image along a line, in two spatial dimensions, in three spatial dimensions, or any of the proceeding as they evolve as a function of time. The image may be an EPID (Electronic Portal Image Device) image, a CT image, a fluoroscopy image, an ultrasound image, a PET image, or an MRI image. This is not intended to limit the scope of the present disclosure. For persons having ordinary skills in the art, a certain number of variations, changes, and/or modifications may be deduced under the guidance of the present disclosure. Those variations, changes, and/or modifications do not depart from the scope of the present disclosure.

According to an aspect of the present disclosure, after a scout image of a subject is obtained, location information of at least one target structure of the subject may be determined based on the scout image. A protocol for performing a procedure regarding the at least one target structure may be determined, according to the location information of the at least one target structure of the subject, by accurately quantifying the location of the at least one target structure identified in the scout image of the subject. According to another aspect of the present disclosure, after a scout image of a subject is obtained, location information of a reference structure of the subject may be determined based on the scout image. An offset between a first position of the subject and a characteristic point of the apparatus may be determined, according to the location information of the reference structure, by accurately quantifying the location of the reference structure identified in the scout image of the subject. The subject may be moved to a second position based on the offset, and a procedure may be performed, using the apparatus, on a target structure of the subject located at the second position. By quantifying the offset of the subject, the efficiency of adjusting the position the subject may be improved, consistency of the position of the subject and the characteristic point (e.g., an imaging center of an imaging scanner) may be improved, and a better imaging quality may be obtained.

Figure 1:
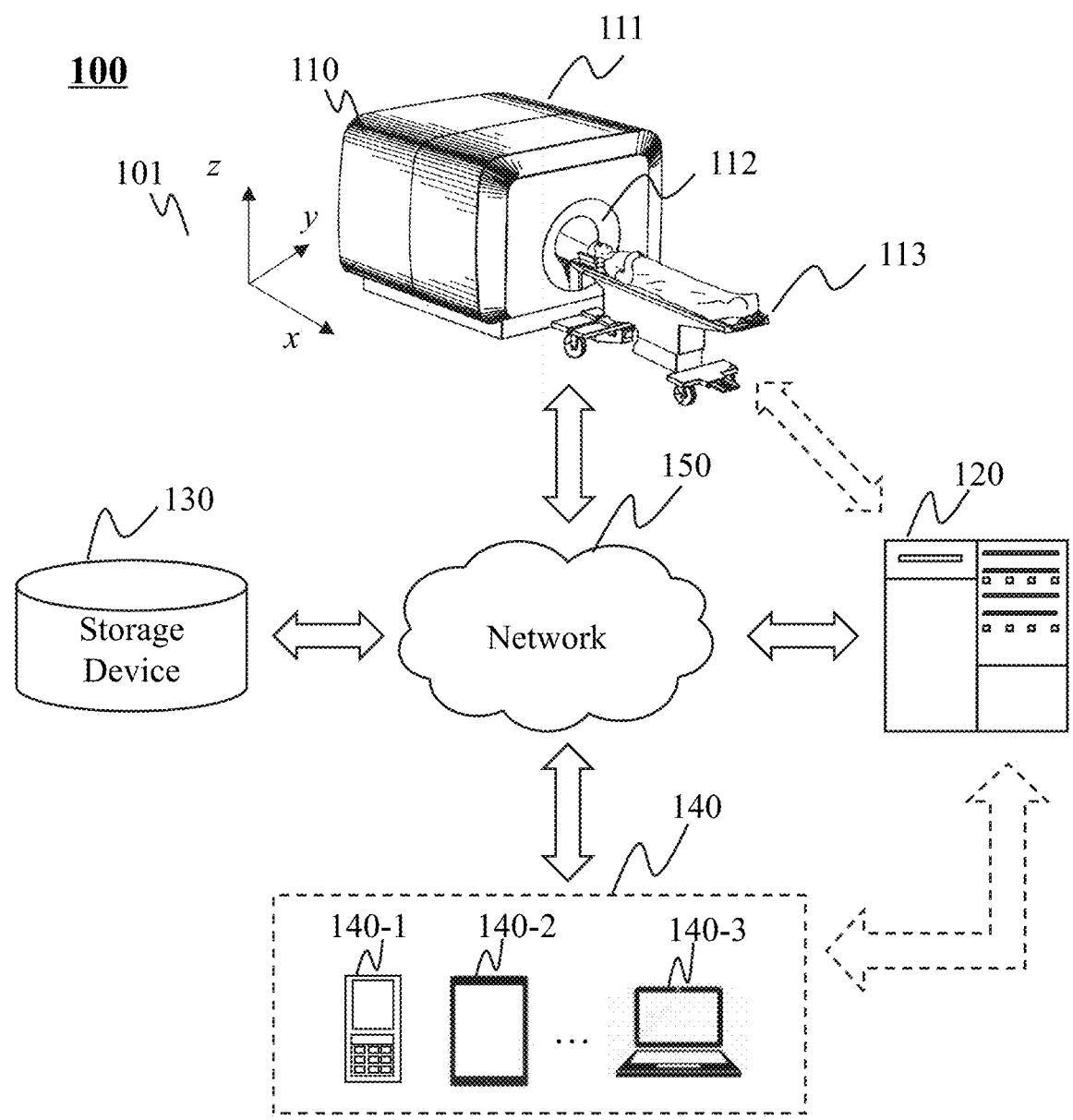
FIG. 1 is a schematic diagram illustrating an exemplary radiation therapy system according to some embodiments of the present disclosure.

FIG. 1 is a schematic diagram illustrating an exemplary imaging system 100 according to some embodiments of the present disclosure. This is understood that the systems and methods for automated positioning of a subject or a portion thereof are also applicable in other systems, e.g., a treatment system. The following descriptions are provided, unless otherwise stated expressly, with reference to an imaging system for illustration purposes and not intended to be limiting. As illustrated, the imaging system 100 may include an imaging scanner 110, a processing device 120, a storage device 130, one or more terminals 140, and a network 150. The components in the imaging system 100 may be connected in various ways. Merely by way of example, as illustrated in FIG. 1, the imaging scanner 110 may be connected to the processing device 120 through the network 150. As another example, the imaging scanner 110 may be connected with the processing device 120 directly as indicated by the bi-directional arrow in dotted lines linking the imaging scanner 110 and the processing device 120. As a further example, the storage device 130 may be connected with the processing device 120 directly (not shown in FIG. 1) or through the network 150. As still a further example, one or more terminal(s) 140 may be connected with the processing device 120 directly (as indicated by the bi-directional arrow in dotted lines linking the terminal(s) 140 and the processing device 120) or through the network 150.

The imaging scanner 110 may scan a subject or a portion thereof that is located within its detection region, and generate imaging signals relating to the (part of) subject. In the present disclosure, the terms "subject" and "object" are used interchangeably. In some embodiments, the subject may include a body, a substance, or the like, or a combination thereof. In some embodiments, the subject may include a specific portion of a body, such as the head, the thorax, the abdomen, or the like, or a combination thereof. In some embodiments, the subject may include a specific organ, such as the heart, the esophagus, the trachea, the bronchus, the stomach, the gallbladder, the small intestine, the colon, the bladder, the ureter, the uterus, the fallopian tube, etc. The imaging scanner 110 may include a computed tomography (CT) scanner, a positron emission computed tomography (PET) scanner, a single-photon emission computed tomography (SPECT) scanner, a magnetic resonance (MR) scanner, an ultrasonic scanner, an emission computed tomography (ECT) scanner, or the like. In some embodiment, the imaging scanner 110 may be a multi-modality device including two or more scanners listed above. For example, the imaging scanner 110 may be a PET-CT scanner, a PET-MR scanner, etc.

Merely for illustration purposes, a PET-CT scanner may be provided as an example for better understanding the imaging scanner 110, which is not intended to limit the scope of the present disclosure. The PET-CT may include a gantry 111, a detecting region 112, and a bed 113. The gantry 111 may support one or more radiation sources and/or detectors (not shown). A subject may be placed on the bed 113 for CT scan and/or PET scan. The PET-CT scanner may combine a CT scanner with a PET scanner. When the imaging scanner 110 performs a CT scan, a radiation source may emit radioactive rays to the subject, and one or more detectors may detect radiation rays emitted from the detecting region 112. The radiation rays emitted from the detecting region 112 may be used to generate CT data (also referred to as CT imaging information). The one or more detectors used in CT scan may include a scintillation detector (e.g., a cesium iodide detector), a gas detector, etc.

To prepare for a PET scan, a radionuclide (also referred to as "PET tracer" or "PET tracer molecules") may be introduced into the subject. The PET tracer may emit positrons in the detecting region 112 when it decays. An annihilation (also referred to as "annihilation event" or "coincidence event") may occur when a positron collides with an electron. The annihilation may produce two gamma photons, which may travel in opposite directions. The line connecting the detector units that detecting the two gamma photons may be defined as a "line of response (LOR)." One or more detector set on the gantry 111 may detect the annihilation events (e.g., gamma photons) emitted from the detecting region 112. The annihilation events emitted from the detecting region 112 may be used to generate PET data (also referred to as PET imaging information). In some embodiments, the one or more detectors used in the PET scan may be different from detectors used in the CT scan. In some embodiments, the one or more detectors used in the PET scan may include crystal elements and photomultiplier tubes (PMT).

The processing device 120 may process data and/or information obtained and/or retrieve from the imaging scanner 110, the terminal(s) 140, the storage device 130 and/or other storage devices. For example, the processing device 120 may obtain pre-scan data from the imaging scanner 110, and reconstruct a scout image of the subject based on the pre-scan data. As another example, the processing device 120 may automatically identify, by processing the scout image, a representation of a target structure of the subject in the scout image, and determine location information of the target structure according to the scout image. As a further example, the processing device 120 may determine, according to the location information of the target structure, an offset of the subject relative to a preset imaging center, or a scanning protocol corresponding to the target structure. In some embodiments, the processing device 120 may be a single server or a server group. The server group may be centralized or distributed. In some embodiments, the processing device 120 may be local or remote. For example, the processing device 120 may access information and/or data stored in the imaging scanner 110, the terminal(s) 140, and/or the storage device 130 via the network 150. As another example, the processing device 120 may be directly connected with the imaging scanner 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented on a computing apparatus 200 having one or more components illustrated in FIG. 2 in the present disclosure.

The storage device 130 may store data and/or instructions. In some embodiments, the storage device 130 may store data obtained from the imaging scanner 110, the terminal(s) 140, and/or the processing device 120. For example, the storage device 130 may store image data, signals, images, videos, algorithms, texts, instructions, program codes, etc. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected with the network 150 to communicate with one or more components of the imaging system 100 (e.g., the processing device 120, the terminal(s) 140, etc.). One or more components of the imaging system 100 may access the data or instructions stored in the storage device 130 via the network 150. In some embodiments, the storage device 130 may be directly connected with or communicate with one or more components of the imaging system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal(s) 140 may remotely operate the imaging scanner 110. In some embodiments, the terminal(s) 140 may operate the imaging scanner 110 via a wireless connection. In some embodiments, the terminal(s) 140 may receive information and/or instructions inputted by a user, and send the received information and/or instructions to the imaging scanner 110 or the processing device 120 via the network 150. In some embodiments, the terminal(s) 140 may receive data and/or information from the processing device 120. In some embodiments, the terminal(s) 140 may be part of the processing device 120. In some embodiments, the terminal(s) 140 may be omitted.

The network 150 may include any suitable network that can facilitate the exchange of information and/or data for the imaging system 100. In some embodiments, one or more components of the imaging system 100 (e.g., the imaging scanner 110, the terminal(s) 140, the processing device 120, or the storage device 130) may communicate information and/or data with one or more other components of the imaging system 100 via the network 150. In some embodiments, the network 150 may be any type of wired or wireless network, or a combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected with the network 150 to exchange data and/or information.

It should be noted that the above description of the imaging system 100 is merely provided for the purposes of illustration, not intended to limit the scope of the present disclosure. For persons having ordinary skills in the art, components contained in the imaging system 100 may be combined or adjusted in various ways, or connected with other components as sub-systems, and various variations and modifications may be conducted under the teaching of the present disclosure. However, those variations and modifications may not depart the spirit and scope of this disclosure. For example, the imaging scanner 110 may be a standalone device external to the imaging system 100, and the imaging system 100 may be connected to or in communication with the imaging scanner 110 via the network 150. All such modifications are within the protection scope of the present disclosure.

FIG. 2 is a schematic diagram illustrating hardware and/or software components of an exemplary computing apparatus 200 on which the processing device 120 may be implemented according to some embodiments of the present disclosure. As illustrated in FIG. 2, the computing apparatus 200 may include a processor 210, a storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the imaging scanner 110, the terminal(s) 140, the storage device 130, and/or any other component of the imaging system 100. Specifically, the processor 210 may process image data obtained from the imaging scanner 110. For example, the processor 210 may generate an image (e.g., a scout image) based on the image data. In some embodiments, the image may be stored in the storage device 130, the storage 220, etc. In some embodiments, the image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing apparatus 200. However, it should be noted that the computing apparatus 200 in the present disclosure may also include multiple processors. Thus operations and/or method steps that are performed by one processor as described in the present disclosure may also be jointly or separately performed by the multiple processors. For example, if in the present disclosure the processor of the computing apparatus 200 executes both operation A and operation B, it should be understood that operation A and operation B may also be performed by two or more different processors jointly or separately in the computing apparatus 200 (e.g., a first processor executes operation A and a second processor executes operation B, or the first and second processors jointly execute operations A and B).

The storage 220 may store data/information obtained from the imaging scanner 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for determining an offset of a subject relative to an imaging center of the imaging scanner 110.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the imaging scanner 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
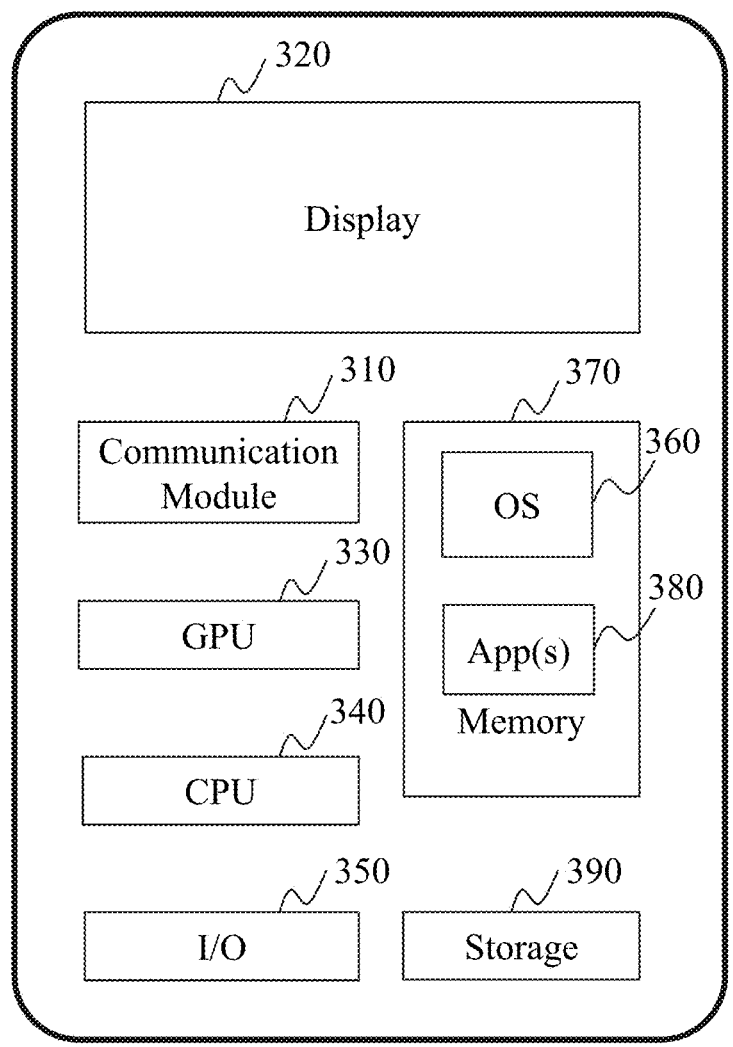
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 370, and a storage 390. In some embodiments, any other suitable component, including but not limited to a system bus or a controller (not shown), may also be included in the mobile device 300. In some embodiments, a mobile operating system 360 (e.g., iOS, Android, Windows Phone, etc.) and one or more applications 380 may be loaded into the memory 370 from the storage 390 in order to be executed by the CPU 340. The applications 380 may include a browser or any other suitable mobile apps for receiving and rendering information relating to data processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an imaging report as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
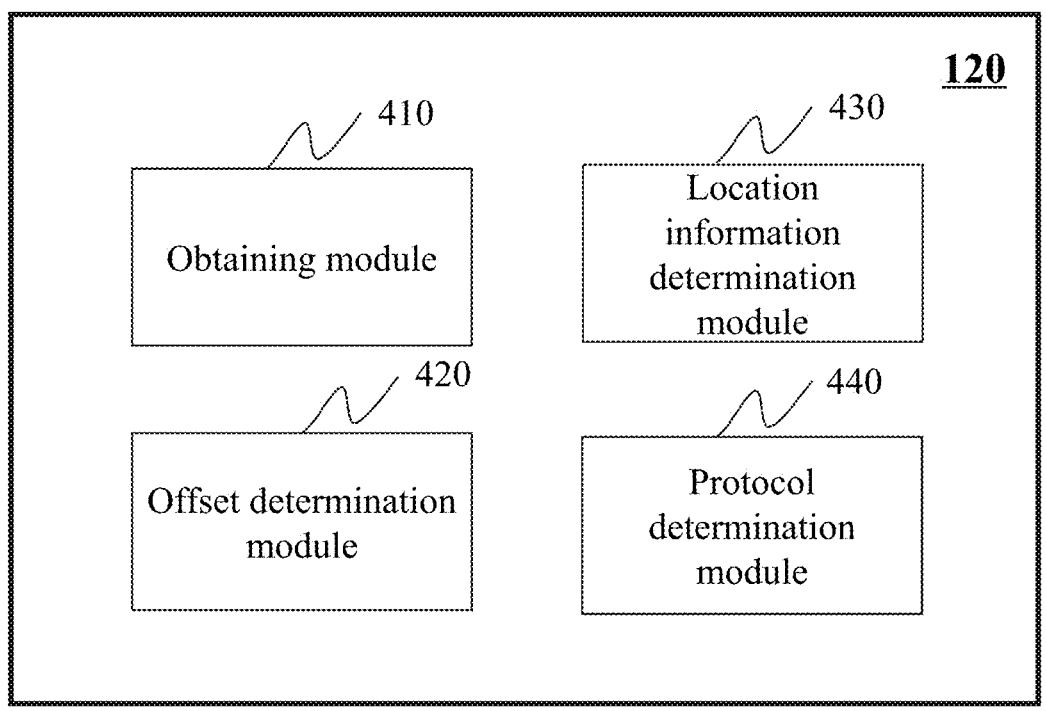
FIG. 4 is a block diagram illustrating an exemplary processing device according to some embodiments of the present disclosure.

FIG. 4 is a block diagram illustrating an exemplary processing device according to some embodiments of the present disclosure. The processing device 120 may include an obtaining module 410, a location information determination module 420, an offset determination module 430, and a protocol determination module 440. One or more of the modules of the processing device 120 may be interconnected. The connection(s) may be wireless or wired. At least a portion of the processing device 120 may be implemented on a computing apparatus as illustrated in FIG. 2 or a mobile device as illustrated in FIG. 3.

The obtaining module 410 may obtain data and/or information. In some embodiments, the obtaining module 410 may obtain the data and/or information from an imaging device (e.g., the imaging scanner 110) or a treatment device. The data and/or information may include an image (e.g., a two-dimensional (2D) image, a three-dimensional (3D) image, etc.), image data (e.g., image data corresponding to an image), or the like.

In some embodiments, the obtaining module 410 may obtain a scout image of the subject. In some embodiments, the imaging system 100 may obtain scanning instructions for generating the scout image of the subject and causing the imaging scanner 110 to perform a positioning scan (i.e., pre-scan) according to the received scanning instructions to generate scout image of the subject. The scanning instructions may be generated according to operations of a user (e.g., a doctor, a technician, etc.).

The location information determination module 420 may determine location information of at least one reference structure or target structure according to the scout image. The reference structure may be a structure of the subject selected for positioning the subject. The target structure may be a structure, for example, specified by a user, to be scanned in an imaging scan. In some embodiments, the target structure may be different from the reference structure.

In some embodiments, the reference structure or the target structure may be identified from the scout image according to a contour of the reference structure or the target structure. For example, a contour of each of multiple structures of the subject in the scout image may be determined. A contour of the reference structure or the target structure of a generalized or standardized subject (e.g., retrieved from a database) may be compared with contours of structures in the scout image. If a similarity between the contour of the reference structure or the target structure of the generalized subject and a contour of a particular structure in the scout image is higher than a preset threshold, the particular structure may be deemed to be the reference structure or the target structure.

In some embodiments, one or more feature points of the reference structure or the target structure may be determined based on the scout image. The one or more feature points of the reference structure or the target structure may include at least one edge point and/or at least one center point. An edge point may refer to a point on a contour of the reference structure or the target structure. In some embodiments, the at least one center point of the reference structure or the target structure may be determined based on the at least one edge point. In some embodiments, the center point may be determined by calculating a center of the reference structure or the target structure using the at least one edge point. In some embodiments, one of the at least one edge point may be designated as a center point. The location information of the reference structure or target structure may be determined based on the one or more feature points of the reference structure or the target structure.

The offset determination module 430 may determine an offset of the subject relative to a characteristic point of an apparatus or an auxiliary offset of the subject according to the location information. The apparatus may include an imaging device or a treatment device. If the apparatus is an imaging device (e.g., the imaging scanner 110), the characteristic point of the apparatus may include an imaging center of the imaging device. If the apparatus is a treatment device, the characteristic point of the apparatus may include an isocenter of the treatment device.

In some embodiments, a distance may be determined based on the location information of the at least one reference structure and the characteristic point of the apparatus. The distance may be determined as the offset of the subject relative to the characteristic point of the apparatus. The position of the subject or a portion thereof may be adjusted from a first location to a second location based on the offset so that an image with a desired or acceptable quality may be obtained. The auxiliary offset of the subject may be determined according to the location information of the target structure and the one or more edges of an imaging-scan region set for the target structure.

For example, if the target structure is the lungs of the subject, and the scout image includes the upper part of the body of the subject, at least one reference structure, such as the head and/or the shoulders of the subject, may be identified in the scout image. The offset of the subject relative to the characteristic point of the apparatus (e.g., the imaging center of the imaging scanner 110) may be determined according to one or more feature points of the head and/or the shoulders and the characteristic point. The auxiliary offset of the subject may be determined according to the location information of the lungs and an imaging-scan region set for the lungs (e.g., a region encompassing the lungs). In this way, the position of the subject may be adjusted to achieve a proper positioning of the at least one reference structure of the subject and the characteristic point according to the offset of the subject relative to the characteristic point, and the position of the lungs may be adjusted according to the auxiliary offset of the subject, thereby obtaining an image of the lungs of the subject with improved quality.

The protocol determination module 440 may determine a protocol for performing a procedure regarding the at least one target structure. In some embodiments, the protocol determination module 440 may determine the protocol according to the location information of the at least one target structure. For an treatment device, the procedure may include performing a treatment on the at least one target structure of the subject. The protocol may be or include a treatment plan. For an imaging device, the procedure may include imaging the at least one target structure of the subject. The protocol may be or include a scanning protocol. In some embodiments, the scanning protocol may include bed information, scanning parameters, etc. the bed information which may include a number or count of bed positions and location information of each bed position. The scanning parameters may be value ranges of parameters of the imaging scanner 110 for scanning a subject.

In some embodiments, protocols for performing procedures regarding target structures of different attributes may be different. Merely by ways of example, the attribute of a target structure may include a dynamic attribute or a static attribute. In an imaging scan, a target structure may be positioned into an overlapping region between two scanning regions corresponding to two adjacent bed positions or an non-overlapping region in a scanning region according to the attribute (dynamic or static) of the target structure. If a target structure is a static structure, coordinates of an upper edge and a lower edge of the target structure in the vertical direction (i.e., a length direction of the bed 113) may be used as coordinates of an upper edge of a first scanning region corresponding to a lower bed position and a lower edge of a second scanning region corresponding to an upper bed position adjacent to the lower bed position, so that the entire target structure may be encompassed in the overlapping region between the first scanning region and the second scanning region. If a target structure is a dynamic structure, a coordinate of a center of the target structure in a vertical direction (i.e., in one dimension) may be used as a coordinate of a center of a scanning region corresponding to a bed position in a vertical direction (i.e., a length direction of the bed 113), so that the entire target structure may be encompassed in a non-overlapping region of a scanning region.

It should be noted that the above descriptions of the processing device 120 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 120 may include one or more other modules. In some embodiments, two or more units in the processing device 120 may form one module. However, those variations and modifications also fall within the scope of the present disclosure.

Figure 5:
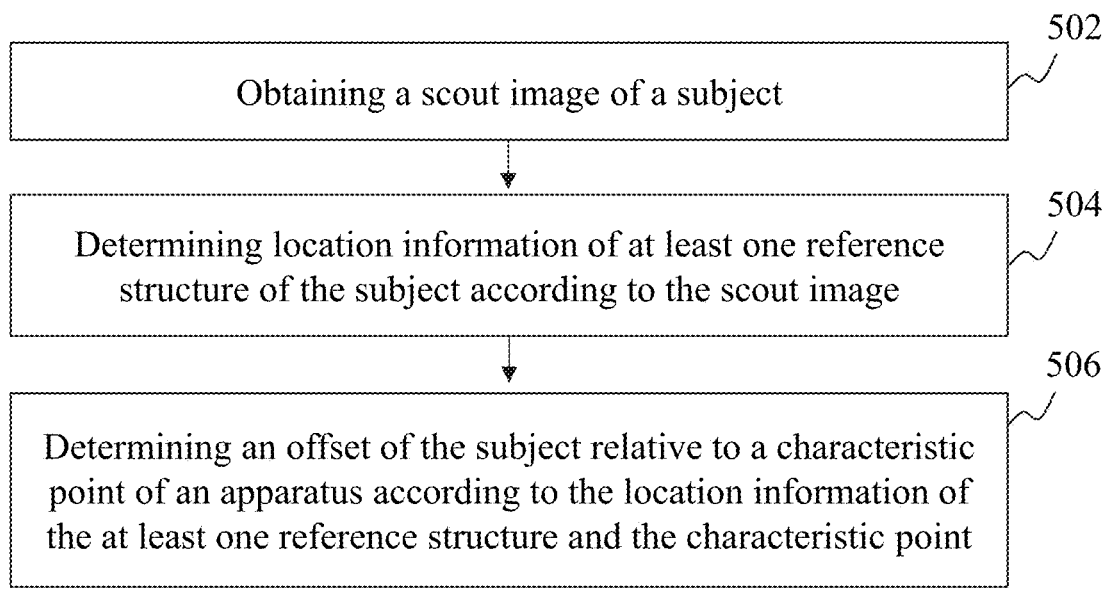
FIG. 5 includes a flowchart illustrating an exemplary process for determining an offset of a subject relative to a characteristic point of an apparatus according to some embodiments of the present disclosure.

FIG. 5 includes a flowchart illustrating an exemplary process for determining an offset of a subject relative to a characteristic point of an apparatus according to some embodiments of the present disclosure. In some embodiments, at least a portion of the process 500 may be performed by the processing device 120 (e.g., implemented in the computing apparatus 200 shown in FIG. 2, the processing device illustrated in FIG. 4). In some embodiments, at least a portion of the process 500 may be performed by a terminal device (e.g., the mobile device 300 shown in FIG. 3) embodying software and/or hardware.

In 502, a scout image of a subject may be obtained. The scout image may be obtained by, for example, the obtaining module 410.

In some embodiments, the imaging system 100 may be a single modality system, such as a positron emission tomography (PET) system, a magnetic resonance (MR) system, a computed tomography (CT) system, a single-photon emission computed tomography (SPECT) system, an X-ray product system, an ultrasound system, a radiation treatment (RT) system, etc. In some embodiments, the imaging system 100 may be a multi-modality system, such as PET-MR system, a PET-CT system, etc.

The imaging system 100 may receive scanning instructions for generating a scout image of the subject and causing the imaging scanner 110 to perform a positioning scan (i.e., pre-scan) according to the received scanning instructions to generate the scout image of the subject. Merely by ways of example, the scanning instructions may be generated when the imaging system 100 receives a user operation (e.g., a manual selection of a region to be scanned). The scanning instructions may include one or more scanning parameters of the imaging scanner 110. In some embodiments, the one or more scanning parameters may include a scanning region, a scanning count, a scanning resolution, or the like, or any combination thereof.

The scanning region may be a region of the subject to be scanned, which may be defined according to default settings of the imaging system 100. The scanning region may be, for example, a whole-body scanning region, a half-body scanning region, etc. In some embodiments, the scanning region may be defined by a user. For example, a user may specify a maximum scanning region of the imaging scanner 110 as the scanning region. The maximum scanning region may refer to an effective region for signal acquisition of the imaging scanner 110. The scanning region may also be referred to as pre-scan region in a pre-scan. As another example, a user may specify a region of the subject as the scanning region.

The scanning count may be the count or number of sub-scans to be performed to implement the scan of the scanning region of the subject. For example, the subject may be scanned using a PET scanner, and scout image data (also referred to as pre-scan data) may be obtained. The scout image data may be projected in any direction to obtain a scout image of the projected direction. For example, the scout image data may be projected in three directions including a sagittal direction, a coronal direction, and a transverse direction to obtain three scout images of the subject. The three scout images may be obtained by performing one positioning scan or multiple positioning sub-scans. As another example, the subject may be scanned by performing one positioning scan or multiple positioning sub-scans (i.e., the scanning count may be one or more) using an MR scanner, and scout images may be generated in the three directions including the sagittal direction, the coronal direction, and the transverse direction.

The scanning resolution may relate to the level of details of structures of the subject acquired in a scan. Since the scout image is used for positioning structures (e.g., specific portions of a body, specific organs, etc.) of the subject rather than medical diagnosis, the scanning resolution may be set to a lower value than a medical image for diagnosis acquired based on the scout image to achieve a fast acquisition of the scout image.

In 504, location information of at least one reference structure of the subject may be determined according to the scout image. The location information may be determined by, for example, the location information determination module 420.

A reference structure may be a structure of the subject selected for facilitating the positioning of the subject. The reference structure may be, for example, the head, a shoulder, a hand, a buttock, the crotch, the spine, a foot, etc., or a combination thereof. In some embodiments, the reference structure may be identified from the scout image according to a contour of the reference structure. For example, a contour of each of multiple structures of the subject in the scout image may be determined. A contour of the reference structure of a generalized or standardized subject (e.g., retrieved from a database) may be compared with contours of structures in the scout image. If a similarity between the contour of the reference structure of the generalized subject and a contour of a particular structure in the scout image is higher than a preset threshold, the particular structure may be deemed to be the reference structure. The contour of each structure of the generalized or standardized subject may be pre-stored in a storage device associated with the imaging system 100 capable of storing data, for example, the storage device 130.

Location information of the reference structure in the scout image may indicate a location of the subject or a target structure of the subject relative to a characteristic point of an apparatus. The target structure may be a structure to be scanned in an imaging scan. In some embodiments, the target structure may be different from the reference structure. An offset of the subject relative to the characteristic point of the apparatus may be determined. The apparatus may include an imaging device or a treatment device. If the apparatus is an imaging device (e.g., the imaging scanner 110), the characteristic point of the apparatus may include an imaging center of the imaging device. If the apparatus is a treatment device, the characteristic point of the apparatus may include an isocenter of the treatment device. Then the location of the subject may be adjusted from a first position to a second position according to the offset of the subject relative to the characteristic point. In this way, the subject may be located within one or more optimal regions of the apparatus (e.g., optimal scanning regions of the imaging scanner 110), thus improving the efficiency on positioning the subject, avoiding repeated readjustments of the location of the subject during imaging, as well as improving the quality of images of the subject acquired when the subject is properly positioned based on the scout image.

In some embodiments, one or more feature points of each of the at least one reference structure may be determined based on the scout image. Coordinates of the one or more feature points may be determined. In some embodiments, the coordinates of the one or more feature points may be determined in a preset coordinate system, for example, the coordinate system 101 illustrated in FIG. 1. In some embodiments, an origin and other parameters (e.g., positive directions of axes) of the preset coordinate system may be defined according to actual needs.

For example, a first pixel at an upper left corner of the scout image may be defined as corresponding to the origin of the preset coordinate system. As illustrated in FIG. 1, the direction pointing to the right when facing the front of the imaging scanner 110 in the horizontal direction may be defined as a positive direction of they axis of the preset coordinate system, and the upward direction in the vertical direction may be defined as a positive direction of the z axis of the preset coordinate system, and the direction pointing from the front of the imaging scanner 110 to outside may be defined as a positive direction of the x axis of the preset coordinate system. In some embodiments, the coordinates of the one or more feature points of each of the at least one reference structure may be determined and included in the location information of the at least one reference structure.

In some embodiments, at least one point on a contour of a reference structure may be selected. The at least one point may be designated as the feature point(s) of the reference structure. The coordinate of a feature point in the preset coordinate system may be determined and included in the location information of the reference structure.

Merely for illustration purposes, feature points of target structures are illustrated in FIGS. 6(*a*) through 6(*c*). FIG. 6(*a*) includes a schematic diagram of a human body according to some embodiments of the present disclosure. FIG. 6(*b*) includes a scout image of the human body generated by scanning the human body using a PET scanner according to some embodiments of the present disclosure. FIG. 6(*c*) includes a scout image of the human body generated by scanning the human body using an MR scanner according to some embodiments of the present disclosure.

In some embodiments, the schematic diagram of the human body illustrated in FIG. 6(*a*) may be an image of general purposes (e.g., an image of a generalized or standardized subject). In some embodiments, the image of the human body illustrated in FIG. 6(*a*) may be a photo of a specific subject. For example, a photo may be taken for a subject when the subject is positioned on the bed 113 for a positioning scan. The photo may be taken by, for example, an optical camera installed on the gantry 111. As shown in FIG. 6(*a*), a black rectangle box 618 may represent a maximum scanning region of the imaging scanner 110. A dotted line 620 along the x axis connecting an upper side and a low side of the black rectangle box 618 as illustrated in FIG. 6(*a*) may represent a line passing through an imaging center of the imaging system 100. A human body may be positioned in the black rectangle box 618 for a positioning scan. At least one reference structure may be determined in the human body. The at least one reference structure may include the head, a shoulder, a hand, an ankle, etc., or a combination thereof. For example, if the at least one reference structure includes the head of the human body, an upper vertex 602, a left extreme point 604, and a right extreme point 606 on the contour of the head may be identified. The identified upper vertex 602, left extreme point 604, and right extreme point 606 on the contour of the head may be designated as feature points of the head of the human body. As another example, if the at least one reference structure includes the shoulders, extreme points 608 and 610 on the contour of the shoulders of the human body may be identified. The extreme points 608 and 610 on the contour of the shoulders may be designated as feature points of the shoulders of the human body. As still another example, if the at least one reference structure includes the hands, extreme points 612 and 614 on the contour of the hands may be identified. The identified extreme points 612 and 614 on the contour of the hands may be designated as feature points of the hands of the human body. As a further example, if the at least one reference structure includes the crotch, a point 616 on the contour of upper thighs connecting two thighs may be identified. The identified point 616 on the contour of upper thighs may be designated as feature points of the crotch of the human body.

In some embodiments, the at least one reference structure in the scout images illustrated in FIG. 6(*b*) and FIG. 6(*c*) may be identified by matching the at least one reference structure represented in FIG. 6(*b*) and FIG. 6(*c*) with the at least one reference structure represented in FIG. 6(*a*). The schematic diagram of the subject illustrated in FIG. 6(*a*) includes an image of a generalized or standardized subject, which may be retrieved from a storage device capable of storing data (e.g., the storage device 130). In some embodiments, the at least one reference structure in the scout images illustrated in FIG. 6(*b*) and FIG. 6(*c*) may be identified using morphological information of the at least one reference structure in FIG. 6(*a*). The morphological information of the at least one reference structure may include, for example, the shape of the contour of the at least one reference structure. For example, if the at least one reference structure in FIG. 6(*a*) includes the head of the human body, and the shape of the contour of the head is close to a circle, a structure with the shape of the contour being close to a circle in FIG. 6(*b*) and FIG. 6(*c*) may be determined as the head of the human body.

Feature points of the at least one reference structure in FIGS. 6(*b*) and 6(*c*) may be determined, and coordinates of the feature points in the preset coordinate system may be determined. In some embodiments, the determination of the feature points of the at least one reference structure in FIG. 6(*b*) and FIG. 6(*c*) may be the same as or similar to the determination of the feature points 602 through 616 in FIG. 6(*a*). The coordinates of the feature points in the preset coordinate system may be designated as at least part of location information of the reference structure. For example, an upper vertex 632, a left extreme point 634, and a right extreme point 636 on the contour of the head in FIG. 6(*b*) and an upper vertex 662, a left extreme point 664, and a right extreme point 666 on the contour of the head in FIG. 6(*c*) may be identified. Coordinates of the identified feature points 632-636 and 662-666 may be determined in the preset coordinate system and designated as at least part of the location information of the head of the human body. In some embodiments, the upper vertex 632 and the upper vertex 662 of the head of the human body may be determined by identifying points on the contour of the head of the human body being closest to the upper sides of the maximum scanning regions in FIG. 6(*b*) and FIG. 6(*c*) (not shown in the figures), respectively. The left extreme point 634 and the left extreme point 664 of the head of the human body may be determined by identifying points on the contour of the head of the human body being closest to the left sides of the maximum scanning regions in FIG. 6(*b*) and FIG. 6(*c*), respectively. The right extreme point 636 and the right extreme point 666 of the head of the human body may be determined by identifying points on the contour of the head of the human body being closest to the right sides of the maximum scanning regions in FIG. 6(*b*) and FIG. 6(*c*), respectively. Similarly, feature points 638-646 in FIG. 6(*b*) and feature points 668-676 in FIG. 6(*c*) may also be determined.

In 506, an offset of the subject relative to the characteristic point of the apparatus may be determined according to the location information of the at least one reference structure and the characteristic point. The offset of the subject relative to the characteristic point may be determined by, for example, the offset determination module 430.

The apparatus may include an imaging device or a treatment device. If the apparatus is an imaging device (e.g., the imaging scanner 110), the characteristic point of the apparatus may include an imaging center of the imaging device. If the apparatus is a treatment device, the characteristic point of the apparatus may include an isocenter of the treatment device. As for an imaging device, configurations and/or imaging modes of different imaging scanners may be different. An imaging center of an imaging scanner may be obtained by determining a location in a maximum scanning region of the imaging scanner with an imaging quality better than the imaging quality of other locations in the maximum scanning region. For example, a center of a PET detector in its length direction (along the x axis as illustrated in FIG. 1) may be determined as an imaging center of a PET scanner. As another example, a location corresponding to a uniform magnetic field and a linear gradient may be determined as an imaging center of an MR scanner. As shown in FIG. 6(*a*), the dotted line 620 may represent the imaging center of the imaging system 100 (or the imaging scanner 110). By performing an imaging scan on a scanning region, which is within a certain range of the imaging center, an image with a acceptable quality may be generated. In some embodiments, a distance may be determined based on the location information of the at least one reference structure and the imaging center. The distance may be determined as the offset of the subject relative to the imaging center. The position of the subject or a portion thereof may be adjusted from a first location to a second location based on the offset so that an image with a desired or acceptable quality may be obtained.

In some embodiments, one or more feature points of a reference structure may include at least one edge point and/or at least one center point. An edge point may refer to a point on a contour of the reference structure. In some embodiments, the at least one center point of the reference structure may be determined based on the at least one edge point. In some embodiments, the center point may be determined by calculating a center of the reference structure using the at least one edge point. In some embodiments, one of the at least one edge point may be designated as a center point.

For example, if the at least one reference structure includes the shoulders of the human body, the extreme points on the contour of the shoulders may be edge points of the shoulders. A midpoint of a line connecting the two extreme points may be determined as the center point of the shoulders. As another example, if the at least one reference structure includes the spine of the human body, a first set of points on the left side contour of the spine and a second set of points on the right side contour of the spine corresponding to the first set of points may be edge points of the spine. A centerline of the spine may be determined based on the first set of points, the second set of points, and a center fitting operation. According to the center fitting operation, a third set of points may be obtained by determining midpoints of lines, each of which connects a point of the first set of points and a corresponding point of the second set of points. A line connecting the third set of points, e.g., sequentially, may be designated as the centerline of the spine. Points on the centerline may be designated as the at least one center point of the spine. As a further example, if the at least one reference structure includes the crotch of the human body, the point on the contour of upper thighs connecting the two thighs may be determined as a feature point. The feature point may be an edge point or a center point of the crotch of the human body.

In some embodiments, the offset of the subject relative to the characteristic point may be determined based on at least one distance between the at least one edge point and/or the at least one center point and the imaging center in the preset coordinate system.

For example, the at least one reference structure includes the shoulders of the human body, the two extreme points and the center point of the shoulder may be determined. In some embodiments, two distances between the two extreme points of the shoulders and the imaging center may be determined. The two distances may be compared to determine whether the two distances are equal. If the two distances are not equal, one half of a difference between the two distances may be determined and designated as the offset of the subject relative to the characteristic point of the apparatus. As another example, a distance between the center point of the shoulders and the preset imaging center may be determined. The distance between the center point of the shoulders and the preset imaging center may be designated as the offset of the characteristic point of the apparatus.

After the offset of the subject relative to the characteristic point of the apparatus is determined, how to adjust the position of the subject from a first position (e.g., the current position) to a second position may be determined according to the offset. For example, if the offset of the subject relative to the imaging center is 5 centimeters towards the left (evaluated based on the positions of the shoulders of the subject), it may be determined that the subject needs to be moved such that the shoulders of the subject are moved 5 centimeters towards the right, thereby positioning the subject at the imaging center of the imaging system 100 (or the imaging scanner 110). In this way, a better imaging quality may be achieved, repeated readjustment of the subject may be avoided, and the efficiency on positioning the subject may be improved. In some embodiments, the adjustment information may be transmitted to a user (e.g., a doctor) from the imaging system 100. The adjustment information may include a text message, a voice message, an optical signal, or the like, or any combination thereof.

The exemplary process 500 for positioning the subject in the imaging system 100 provided in the present disclosure may provide the offset of the subject relative to the characteristic point of the apparatus by quantifying the location of the at least one reference structure identified in the scout image of the subject. By quantifying the offset of the subject, the efficiency of adjusting the position the subject may be improved, the consistency of the position of the subject and the characteristic point (e.g., the imaging center of the imaging scanner) may be improved, and a better imaging quality may be obtained.

Figure 7:
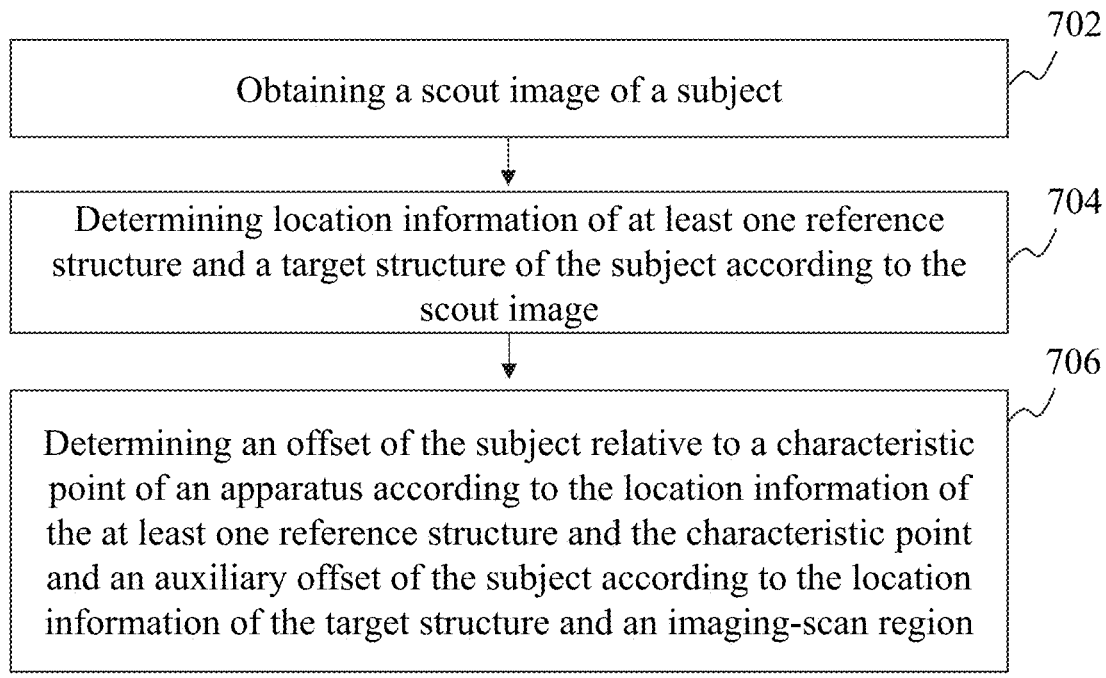
FIG. 7 includes a flowchart illustrating an exemplary process for determining an offset of a subject relative to a characteristic point of an apparatus and an auxiliary offset of the subject according to some embodiments of the present disclosure.

FIG. 7 includes a flowchart illustrating an exemplary process for determining an offset of a subject relative to a characteristic point of an apparatus and an auxiliary offset of the subject according to some embodiments of the present disclosure. In some embodiments, at least a portion of the process 700 may be performed by the processing device 120 (e.g., implemented in the computing apparatus 200 shown in FIG. 2, the processing device illustrated in FIG. 4, etc.). In some embodiments, at least a portion of the process 700 may be performed by a terminal device (e.g., the mobile device 300 shown in FIG. 3) embodying software and/or hardware.

In 702, a scout image of a subject may be obtained. In some embodiments, the operation 702 may be performed by the obtaining module 410. The scout image may be generated by performing a positioning scan or multiple positioning sub-scans on the subject. In some embodiments, the operation 702 may be the same as or similar to the operation 502.

In 704, location information of at least one reference structure and an target structure of the subject may be determined according to the scout image. In some embodiments, the location information of at least one reference structure and the target structure of the subject may be determined by the location information determination module 420. The target structure may be a body part of the subject to be scanned in an imaging scan.

The target structure may include, for example, the head, a lung, the heart, the liver, the bladder, or the like, or any combination thereof. In some embodiments, the target structure may be designated as a region of interest (ROI). In some embodiments, the imaging system 100 (e.g., the imaging scanner 110) may perform an imaging scan on the ROI after the positioning scan is performed. For example, the imaging system 100 (e.g., the imaging scanner 110) may further scan the lungs of the subject after the positioning scan is performed. In some embodiments, the ROI may be scanned to obtain image data of the ROI, and an image of the ROI may be reconstructed based on the image data of the ROI. In some embodiments, a dose of a treatment medium may be delivered to the ROI instead of performing the imaging scan on the ROI. For example, a radiation dose may be delivered to the liver of the subject in a radiotherapy for treating liver cancer.

In 706, an offset of the subject relative to a characteristic point of an apparatus may be determined according to the location information of the at least one reference structure and the characteristic point, and an auxiliary offset of the subject may be determined according to the location information of the target structure and an imaging-scan region. The offset and the auxiliary offset may be determined by the offset determination module 430. In some embodiments, the determination of the offset of the subject relative to the characteristic point of an apparatus may be the same as or similar to the operation 506 in the process 500 as illustrated in FIG. 5.

Before the imaging system 100 scans the target structure, an imaging-scan region may be determined based on the scout image. The imaging-scan region may be a region that the imaging scan is (to be) performed. In some embodiments, the imaging-scan region may encompass the imaged structure. The auxiliary offset of the subject may represent an offset of the target structure (e.g., at least one center point and/or at least one edge point of the target structure) relative to a characteristic point (e.g., a center or one or more edges of the imaging-scan region). In some embodiments, the auxiliary offset of the subject may be determined according to the location information of the target structure and the imaging-scan region in the scout image. In this way, the position of the target structure may be further adjusted so as to improve imaging quality of the target structure.

The sequence of the determination of the location information of the at least one reference structure and the determination of the location information of the target structure may not be specifically limited. For example, the determination of the location information of the at least one reference structure may be performed before the determination of the location information of the target structure. As another example, the determination of the location information of the at least one reference structure may be performed after the determination of the location information of the target structure. As a further example, the determination of the location information of the at least one reference structure and the determination of the location information of the target structure may be performed at a same time. Similarly, the sequence of the determination of the offset of the subject relative to the characteristic point and the determination of the auxiliary offset of the subject may not be specifically limited.

In some embodiments, the target structure may be the same as the at least one reference structure or a part of the at least one target structure. The offset of the subject relative to the characteristic point may be determined according to the location information of the at least one reference structure and the characteristic point. The auxiliary offset of the subject may be determined according to the location information of the at least one reference structure and one or more edges of the imaging-scan region. For example, if the target structure is the head of the subject, and the head of the subject is also a reference structure, one or more feature points of the head of the subject may be obtained. The offset of the subject relative to the characteristic point (e.g., the imaging center of the imaging scanner 110) may be determined according to distances between the one or more feature points and the characteristic point. The auxiliary offset of the subject may be determined according to distances between the one or more feature points and the one or more edges of an imaging-scan region set for the head of the subject, such that the position of the head of the subject may be adjusted, e.g., from the first position to the second position, according to the offset and the auxiliary offset of the subject to obtain a scanning image of the head with improved quality.

In some embodiments, the target structure may be different from the at least one reference structure. The offset of the subject relative to the characteristic point may be determined according to the location information of the at least one reference structure and the characteristic point. The auxiliary offset of the subject may be determined according to the location information of the target structure and the one or more edges of the imaging-scan region. For example, if the target structure is the lungs of the subject, and the scout image may include the upper part of the body of the subject, at least one reference structure, such as the head and/or the shoulders of the subject, may be identified in the scout image. The offset of the subject relative to the characteristic point of the apparatus (e.g., the imaging center of the imaging scanner 110) may be determined according to one or more feature points of the head and/or the shoulders and the characteristic point. The auxiliary offset of the subject may be determined according to the location information of the lungs and an imaging-scan region set for the lungs (e.g., a region encompassing the lungs). In this way, the position of the subject may be adjusted to achieve a proper positioning of the at least one reference structure of the subject and the characteristic point according to the offset of the subject relative to the characteristic point, and the position of the lungs may be adjusted according to the auxiliary offset of the subject, thereby obtaining an image of the lungs of the subject with improved quality.

In some embodiments, the imaging-scan region may be set by a user (e.g., a doctor) according to clinical experience. In some embodiments, the imaging-scan region may be set by the imaging system 100 according to one or more features of the target structure and/or the subject. For example, the imaging-scan region may be set by the imaging system 100 according to a height, a weight, a head circumference and/or a shoulder breadth of the subject dynamically.

In some embodiments, one or more feature points of the target structure may be selected. The one or more feature points may include at least one edge point and/or at least one center point. The at least one center point may be determined by calculating a center of the target structure using the at least one edge point. The auxiliary offset of the subject may be determined according to distances between the one or more feature points of the target structure and a center or one or more edges of the imaging-scan region. For example, if the target structure is the heart of the subject, one or more feature points of the heart may be selected. A determination as to whether an image including the entire heart may be made according to relative locations of the feature points and an imaging-scan region set for the heart of the subject. And another determination as to whether the image of the heart has a good quality may be made according to distances between a center point of the heart and a center or one or more edges of the imaging-scan region. In some embodiments, the determination of the auxiliary offset of the subject may be similar to the determination of the offset of the subject relative to the characteristic point.

In some embodiments, the location information of the at least one reference structure corresponding to the target structure in the scout image may be determined as the location information of the target structure. In some cases, it may be difficult to extract a contour of the target structure, and the location information of the at least one reference structure corresponding to the target structure may be used as the location information of the target structure. For example, if the target structure is the bladder of the subject, and it may be difficult to extract the contour of the bladder, location information of the crotch of the subject corresponding to the bladder may be used as the location information of the bladder, and the location information of the crotch may be used to determine the auxiliary offset of the subject. In some embodiments, a relationship between the target structure and the at least one reference structure may be pre-established. After at least one reference structure corresponding to a target structure is selected, the auxiliary offset of the subject may be determined according to distance(s) between a center point of the at least one reference structure and the center or one or more edges of the imaging-scan region.

The exemplary process for positioning the subject in the imaging system 100 provided in the process 700 may provide an improvement to the process 500. After the offset of the subject relative to the characteristic point is determined according to the location information of the reference structure, the imaging system 100 may further perform an imaging scan on the target structure, and the auxiliary offset of the subject may be further determined according to the location information of the target structure and an imaging-scan region encompassing the target structure.

Figure 8:
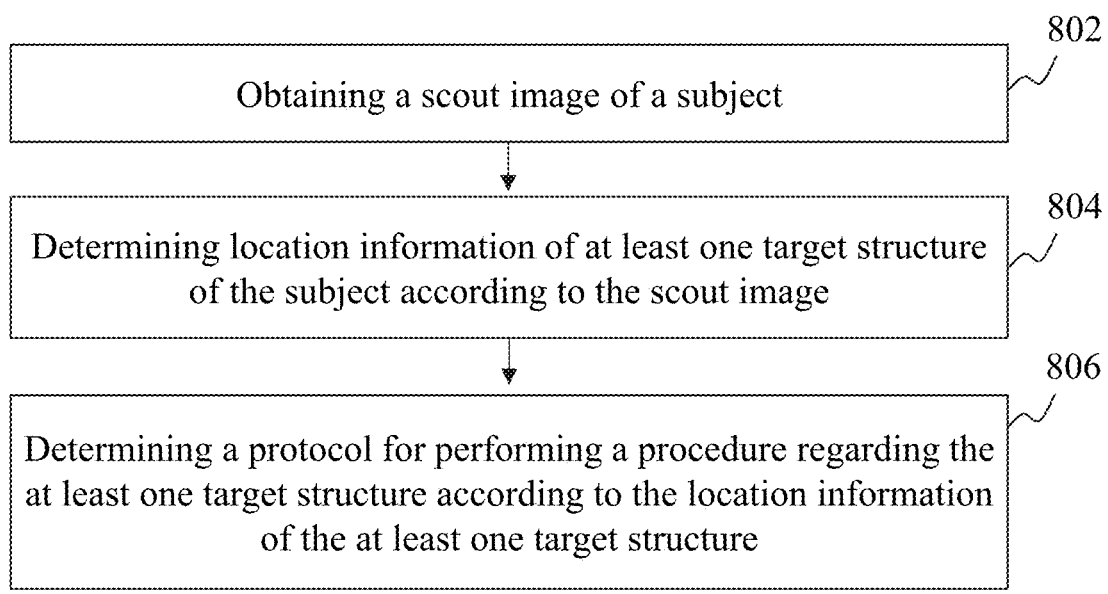
FIG. 8 includes a flowchart illustrating an exemplary process for determining a protocol for performing a procedure in an imaging scan according to some embodiments of the present disclosure.

FIG. 8 includes a flowchart illustrating an exemplary process for determining a protocol for performing a procedure in an imaging scan according to some embodiments of the present disclosure. The process 800 may be applicable to cases in which multiple scanning regions corresponding to different bed positions are determined in the protocol. In some embodiments, at least a portion of the process 800 may be performed by the processing device 120 (e.g., implemented in the computing apparatus 200 shown in FIG. 2, the processing device illustrated in FIG. 4, etc.). In some embodiments, at least a portion of the process 800 may be performed by a terminal device (e.g., the mobile device 300 shown in FIG. 3) embodying software and/or hardware.

In 802, a scout image of a subject may be obtained. The scout image of the subject may be obtained by, for example, the obtaining module 410. In some embodiments, the operation 802 may be the same as or similar to the operation 502 of the process 500 as illustrated in FIG. 5.

In order to obtain an image with high quality, a protocol for performing a procedure regarding a target structure of the subject may be determined based on a location of the target structure. Therefore, a scout image of the subject may be obtained before the protocol is determined, and location information of the target structure may be determined based on the scout image.

In some embodiments, the imaging system 100 may obtain scanning instructions for generating a scout image of the subject and causing the imaging scanner 110 to perform a positioning scan (i.e., pre-scan) according to the received scanning instructions to generate the scout image of the subject. A pre-scan region including the target structure may be determined according to the scanning instructions. In some embodiments, the scanning instructions may be generated according to operations of a user (e.g., a doctor, a technician, etc.).

The imaging system 100 may direct, according to the scanning instructions, an imaging scanner (e.g., the imaging scanner 110) to scan the pre-scan region so as to obtain pre-scan data. In some embodiments, the scanning of the pre-scan region may be implemented using at least one imaging modality. An imaging modality may relate to an imaging scanner of a certain type (e.g., a CT scanner, a PET scanner, an MR scanner, etc.). In some embodiments, each type of scanner may correspond to an imaging modality. The imaging system 100 may reconstruct one or more images of the pre-scan region based on the pre-scan data. The one or more images of the pre-scan region may be designated as the scout image. For example, the imaging system 100 may reconstruct two or more images of the pre-scan region based on the pre-scan data. The scout image of the pre-scan region may be generated by splicing the two or more images in a particular manner.

In some embodiments, the pre-scan region may be determined according to operation instructions input by the user. For example, the user may specify a pre-scan region directly on an operation interface of a terminal device (e.g., the I/O 350 of mobile device 300). In some embodiments, the imaging system 100 may resolve an operation region from the operation instructions input by the user, and designate the operation region resolved from the operation instructions as the pre-scan region. For example, if it is needed to obtain an image of the whole body of the subject, a "whole body scan" option may be selected in the operation interface, and scanning instructions corresponding to the "whole body scan" option may be generated. After the imaging system 100 obtains the scanning instructions, the scanning instructions may be resolved, an operation region of "whole body" may be resolved from the scanning instructions, and the "whole body" of the subject may be designated as the pre-scan region.

In some embodiments, the pre-scan region may be determined based on at least one target structure specified by a user. Merely for illustration purposes, the user may select a structure of interest (e.g., the head, the neck, a lung, the heart, the liver, the bladder, etc.) in the operation interface. Scanning instructions, for example, in forms of computer readable programs or codes, may be generated based on the selection of the user. After the imaging system 100 obtains the scanning instructions, the structure of interest may be resolved from the scanning instructions and designated as the target structure. It may be understood that the user may specify a plurality of ROIs, and the plurality of ROIs may be designated as the at least one target structure. The location(s) of the at least one target structure may be obtained. The pre-scan region may be determined based on the location(s) of the at least one target structure.

In some embodiments, a correspondence relationship between target structures and pre-scan regions may be established. The pre-scan region corresponding to the target structure may be determined based on the correspondence relationship. In some embodiments, a minimum region among regions encompassing the at least one target structure may be determined as the pre-scan region.

Merely by ways of example, when the user needs to obtain an image including the head and the lungs of the subject, options "head" and "lungs" may be selected as ROIs by the user through the operation interface, and scanning instructions regarding the ROIs may be generated. The imaging system 100 may obtain and resolve the scanning instructions, and determine the "head" and the "lungs" as the at least one target structure. The imaging system 100 may further determine a pre-scan region including the "head" and the "lungs" of the subject (e.g., an upper part of the body of the subject). The imaging system 100 may perform a pre-scan on the pre-scan region, obtain pre-scan data of the pre-scan region, and generate an image (i.e., the scout image) of the pre-scan region based on the obtained pre-scan data.

In some embodiments, signal acquisition of multiple scanning regions corresponding to multiple bed positions may be implemented by a multi-modality device. If a pre-scan is performed by a multi-modality device, the subject may be scanned using one imaging modality or two or more imaging modalities. Taking a PET-CT scanner as an example, the PET-CT scanner may include a CT scanner and a PET scanner, and the pre-scan region may be scanned using the CT scanner to obtain a scout image of the pre-scan region or both the PET scanner and the CT scanner to obtain two scout images of the pre-scan region. In some embodiments, the pre-scan may be performed using two or more imaging modalities, thus obtaining more detailed structures more accurate location information of the target structure than using a single imaging modality.

In 804, location information of at least one target structure of the subject may be determined according to the scout image. The location information of at least one target structure of the subject may be determined by, for example, the location information determination module 420.

In some embodiments, a target structure may be an ROI specified by the user, for example, through the operation interface. In some embodiments, the target structure may be determined according to the pre-scan region. For example, a correspondence relationship between target structures and pre-scan regions may be established. After a pre-scan region is determined, a target structure corresponding to the pre-scan region may be determined based on the correspondence relationship between target structures and pre-scan regions.

In some embodiments, after the scout image is obtained, the location information of the at least one target structure in the scout image may be obtained by identifying the at least one target structure from the scout image. In some embodiments, the location information of the target structure may be or include coordinates of at least one edge point and/or at least one center point of the target structure in the scout image. For example, the location information of the head of the subject may include coordinates of an upper vertex of the head in the scout image (e.g., in two dimensions or three dimensions). As another example, the location information of the liver of the subject may include coordinates of a center of the liver and one or more edge points on a contour of the liver in the scout image. As a further example, the location information of the neck of the subject may include coordinates of a center point of the neck in the scout image.

In some embodiments, two or more scout images may be obtained. Merely for illustration purposes, if the pre-scan region is scanned using an MR scanner, pre-scan data may be obtained, and scout images in three directions including the sagittal direction, the coronal direction, and the transverse direction may be generated based on the pre-scan data. In some embodiments, a preset number (or count) of images including detailed structural information may be determined as scout images for determining the location information of the at least one target structure. Scout images of a right sagittal direction and an anterior coronal direction may contain more structural information, and the scout images of the right sagittal direction and the anterior coronal direction may be used to determine the location information of the at least one target structure. If the pre-scan region is scanned using a PET scanner, pre-scan data may be obtained, and a scout image may be generated based on the pre-scan data. The scout image may be a three-dimensional (3D) scout image, which may be used for identifying the at least one target structure, and determining location information of the at least one target structure.

In some embodiments, the location of each of the at least one target structure in the scout image may be determined based on structural information of the at least one target structure. For example, each target structure may be identified from the scout image based on morphological information and a signal strength corresponding to the each target structure. The morphological information of each target structure may include, for example, the shape of the contour of the target structure. The signal strength corresponding to each target structure may be an amplitude of a signal regarding the target structure acquired by the imaging scanner 110.

In some embodiments, the location information of the at least one target structure may be determined using a machine learning algorithm. For a certain imaging modality, a plurality of historical scout images of one or more subjects may be obtained. The plurality of historical scout images may be labeled by marking each target structure in the plurality of historical scout images with an identifier. In some embodiments, the plurality of historical scout images may be labeled manually by a user (e.g., a technician). Location information of the labeled target structures in the plurality of historical scout images may be obtained. The plurality of historical scout images and location information of labeled target structures in the plurality of historical scout image (e.g., identifiers corresponding to the labeled target structures and coordinates of the labeled target structures) may be determined as training sample pairs. The imaging system 100 may obtain a structure identification model for determining location information of at least one target structure in a scout image. The structure identification model may be trained using the training sample pairs to obtain a trained structure identification model. The imaging system 100 may input a scout image including at least one target structure into the trained structure identification model, and obtain the output of the trained structure identification model as location information of the at least one target structure.

In some embodiments, a width of the bed 113 may have a fixed value, indicating that a dimension of a scanning region may be fixed in a width direction of the bed. The scanning region may be shifted along the x axis with reference to the coordinate system 101 illustrated in FIG. 1 by moving the bed 113 along the length direction of the bed 113. In this case, vertical coordinates (i.e., a coordinates in the length direction of the bed 113) of one or more edge points and/or center points of the at least one target structure may be used as location information of the at least one target structure.

In 806, a protocol for performing a procedure regarding the at least one target structure may be determined according to the location information of the at least one target structure. The protocol may be determined by, for example, the protocol determination module 440.

In some embodiments, after the location information of the at least one target structure is determined, the protocol for performing a procedure regarding the at least one target structure may be determined according to the location information of the at least one target structure. For an treatment device, the procedure may include performing a treatment (e.g., delivering a dose of a treatment medium) on the at least one target structure of the subject. The protocol may be or include a treatment plan. For an imaging device, the procedure may include imaging the at least one target structure of the subject. The protocol may be or include a scanning protocol.

Merely for illustration purposes, the following descriptions are provided, unless otherwise stated expressly, with reference to the imaging system 100 and not intended to be limiting. The protocol may include bed information, scanning parameters, etc. In some embodiments, the bed information may include a number or count of bed positions and location information of each bed position. The scanning parameters may be value ranges of parameters of the imaging scanner 110 for scanning a subject. It should be understood that different imaging modalities may correspond to different scanning parameters. For example, if the imaging scanner 110 is an MR scanner, the scanning parameters may include shimming parameters of a main magnetic field $B_0$, a radio frequency (RF) magnetic field $B_1$, and/or a frequency calibration parameter. If the imaging scanner 110 is a PET scanner or a CT scanner, the scanning parameters may include an attenuation correction parameter.

In some embodiments, protocols for performing procedures regarding target structures of different attributes may be different. In some embodiments, the attribute of a target structure may include a dynamic attribute or a static attribute. The dynamic attribute may associate with dynamic structures (e.g., organs of the subject such as the liver, the heart, etc.), which are affected by physiological factors (e.g., breathing, heartbeat). The static attribute may associate with static structures (e.g., body parts of the subject such as the head, the pelvis, lower limbs, etc.), which are less affected by the physiological factors. Merely by ways of example, for dynamic structures, multiple sets of image data generated by repeatedly scanning dynamic structures (e.g., the chest, the abdomen) may be obtained for motion correction of images of the dynamic structures so as to improve the quality of the images of the dynamic structures. For static structures, after one set of image data generated upon one scan on the static structure may be obtained, and an image of the static structure may be reconstructed based on the one set of image data. The protocol corresponding to a dynamic structure may be referred to as a dynamic protocol. The dynamic protocol may correspond to a dynamic image reconstruction algorithm related to motion correction. The protocol corresponding to a static structure may be referred to as a static protocol. A static protocol may correspond to a static image reconstruction algorithm (e.g., a conventional image reconstruction algorithm such as a filtered backprojection algorithm for reconstructing a CT image). According to the attribute (dynamic or static) of a target structure, the protocol corresponding to the target structure and the image reconstruction algorithm corresponding to the protocol may be determined to reconstruct an image with high quality. In some embodiments, the protocol may be adaptively adjusted according to a bed position of the target structure, thus achieving a dynamic reconstruction of physiological signals of the target structure or a functional imaging (e.g., a functional imaging of neurons). In some embodiments, the attribute of the target structure and a correspondence relationship between target structures and scanning parameters may be set in advance by a user, according to default settings of the imaging system 100. Scanning parameters of the at least one target structure may be determined based on the correspondence relationship.

In some embodiments, the bed position may be adjust according to the location information of the target structure adaptively, such that a scanning region corresponding to the bed position may encompass the entire target structure (e.g., the head, the neck, the liver, etc.). In this way, different target structures of the subject may be separated clearly, and customized scanning parameters for different target structures may be determined. For example, a motion correction may be performed on a dynamic structure.

FIG. 9 is a schematic diagram of an exemplary imaging scan with automated positioning of a subject according to some embodiments of the present disclosure. Taking a PET-MR scanner as an example, the imaging scan with automated positioning may include two stages 902 and 904. In a first stage 902, accurate locations of one or more target structures of the subject may be obtained according to one or more scout images of the subject. At least one pre-scan regions including the one or more target structures may be scanned to generate the one or more scout images. A PET image 906 and an MR image 908 may be generated by scanning the at least one pre-scan region using a PET scanner and an MR scanner, respectively. Accurate locations (e.g., vertical coordinates along the x axis in the coordinate system 101) of the target structures may be determined according to the PET image 906 and the MR image 908. The one or more target structures may include, for example, the head 910, the neck 912, the heart 914, the liver 916, the bladder 918, the hands 920, and the knees 922. The determined locations of the target structures may be designated as location information of the target structures.

In the second stage 904, scanning parameters corresponding to each target structure may be determined according to the location information of the each target structure. In some embodiments, the scanning parameters may be determined by determining bed positions, scanning regions corresponding to the bed positions, and/or overlap regions of two adjacent scanning regions corresponding to two adjacent bed positions. As shown in FIG. 9, bed positions may be determined according to the location information of the at least one target structure. Scanning regions corresponding to the bed positions may be determined. Overlapping regions of two scanning regions corresponding to two adjacent bed positions may be determined. For example, bed positions 924 and 926 may be determined according to the location information of the at least one target structure. Two scanning regions (e.g., including a scanning region 928) corresponding to the two bed positions 924 and 926 may be determined. An overlapping region 930 of the two scanning regions may be determined. In some embodiments, the target structure may be positioned into an overlapping region between two scanning regions corresponding to two adjacent bed positions or an non-overlapping region in a scanning region according to the attribute of the target structure.

The exemplary operations provided in the present disclosure includes obtaining a scout image of a subject, determining location information of at least one target structure based on the scout image, and determining a protocol for performing a procedure regarding the at least one target structure according to the location information of the at least one target structure. The location information of the at least one target structure may be determined by identifying the at least one target structure from the scout image. In this way, an imaging scan with accurate and fast positioning of the subject may be realized. The manner in which the subject is scanned may be more efficient, the imaging quality may be improved. In addition, protocols for different target structures may be determined adaptively so as to realize a customized optimization of the imaging of each target structure such as a dynamic reconstruction physiological signals or a functional imaging.

Figure 10:
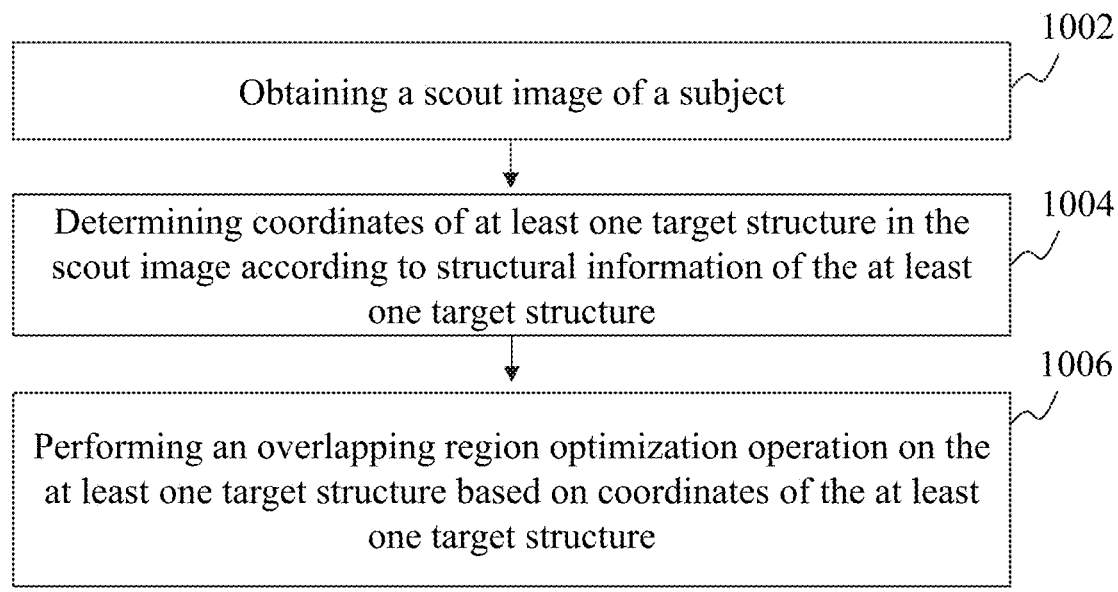
FIG. 10 includes a flowchart illustrating an exemplary process for performing an overlapping region optimization operation in an imaging scan according to some embodiments of the present disclosure.

FIG. 10 includes a flowchart illustrating an exemplary process for performing an overlapping region optimization operation in an imaging scan according to some embodiments of the present disclosure. In some embodiments, at least a portion of the process 1000 may be performed by the processing device 120 (e.g., implemented in the computing apparatus 200 shown in FIG. 2, the processing device illustrated in FIG. 4, etc.). In some embodiments, at least a portion of the process 1000 may be performed by a terminal device (e.g., the mobile device 300 shown in FIG. 3) embodying software and/or hardware.

In 1002, a scout image of a subject may be obtained. The scout image may be generated by performing a positioning scan on the subject. In some embodiments, the operation 1002 may be the same as or similar to the operations 502, 702, and 802 in the processes 500, 700, and 800, respectively.

In 1004, coordinates of at least one target structure in the scout image may be determined according to structural information of the at least one target structure. In some embodiments, the coordinates of the at least one target structure may be designated as location information of the at least one target structure.

In some embodiments, the at least one target structure may be identified from the scout image based on the structural information. The structural information of the a target structure may include morphological information of the target structure and/or a signal strength corresponding to the target structure. The morphological information of each target structure may include, for example, a shape of a contour of the target structure. Different target structures may have different morphological information. The signal strength corresponding to each target structure may be an amplitude of a signal regarding the target structure acquired by the imaging scanner 110. For a certain imaging modality, signal intensities of target structures may be within a certain value range. In some embodiments, morphological information and signal intensities corresponding to different target structures of a generalized or standardized subject may be pre-stored in a storage device (e.g., the storage device 130). For each structure in the scout image, edge information (i.e., information of the contour of the structure) of the structure may be extracted. In some embodiments, the edge information of the structure may be extracted using an edge extraction algorithm or a center extraction algorithm. Morphological information formed by the extracted edge information of the structure may be compared with pre-stored morphology information of target structures. And a signal intensity on the edge of the structure may be compared with the pre-stored signal intensity of target structures. If the morphological information formed by the edge information of a structure matches pre-stored morphological information of a target structure, and the signal strength of the structure is also within a signal strength range of the target structure, the structure may be designated as the target structure.

In 1006, an overlapping region optimization operation may be performed on the at least one target structure based on coordinates of the at least one target structure.

In some embodiments, different overlapping region optimization operations may be performed on target structures of different attributes. Merely for illustration purposes, a target structure may be positioned into an overlapping region between two scanning regions corresponding to two adjacent bed positions or an non-overlapping region in a scanning region according to the attribute (dynamic or static) of the target structure. In some embodiments, the attribute(s) of the at least one target structure may be acquired from a table storing attributes of structures of a subject in a storage device (e.g., the storage device 130).

Merely by ways of example, the liver, the heart, the lungs, and the abdomen of the subject may be determined as dynamic structures, and the head, the neck, the bladder, and the hands of the subject may be determined as static structures. If a target structure is a static structure, coordinates of an upper edge and a lower edge of the target structure in the vertical direction (i.e., a length direction of the bed 113) may be used as coordinates of an upper edge of a first scanning region corresponding to a lower bed position and a lower edge of a second scanning region corresponding to an upper bed position adjacent to the lower bed position. In this case, the entire target structure may be encompassed in the overlapping region between the first scanning region and the second scanning region.

In order to maximize the signal intensity of a static structure, the static structure may be positioned in an overlapping region between two scanning regions corresponding to two adjacent bed positions. The overlapping region may be scanned in two or more sub-scans (i.e., scanned for two or more times), and two or more signals of the static structure may be obtained. An image of the static structure may be obtained through a signal superposition operation of the two or more signals. In some embodiments, coordinates of an upper edge and a lower edge of the target structure in a vertical direction may be used as coordinates of an upper edge of a first scanning region corresponding to a lower bed position and a lower edge of a second scanning region corresponding to an upper bed position adjacent to the lower bed position. In this case, the entire target structure may be encompassed in the overlapping region between the first scanning region and the second scanning region. It may be understood that the upper edge of the target structure may correspond to the upper edge of the first scanning region corresponding to the lower bed position. The lower edge of the target structure may correspond to the lower edge of the second scanning region corresponding to the upper bed position. For example, the coordinates of the upper edge of the target structure may correspond to the coordinates of the upper edge of the first scanning region corresponding to the lower bed position. The coordinates of lower edge of the target structure may correspond to the coordinates of lower edge of the second scanning region corresponding to the upper bed position.

If a target structure is a dynamic structure, a coordinate of a center of the target structure in a vertical direction may be used as a coordinate of a center of a scanning region corresponding to a bed position in a vertical direction (i.e., a length direction of the bed 113). In this case, the entire target structure may be encompassed in a non-overlapping region of a scanning region.

If a dynamic structure is positioned in an overlapping region between two scanning regions corresponding to two adjacent bed positions, signals of the dynamic structure obtained in the two scanning regions may be different due to the motion of the dynamic structure, which may result in poor imaging quality. Therefore, the dynamic structure may need to be positioned in the non-overlapping region of a scanning region, such that the dynamic structure may be scanned for one time in a multi-bed position scan.

In some embodiments, the coordinate of the center of the target structure in the vertical direction may be used as the coordinate of the center of the scanning region. In this case, at least a large part of the target structure may be encompassed in the non-overlapping region. In some embodiments, coordinates of a center, an upper edge, and a lower edge of the dynamic structure may be determined. A determination may be made as to whether the entire dynamic structure is encompassed in the non-overlapping region of a scanning region based on the coordinates of the center, the upper edge, and the lower edge of the dynamic structure.

The exemplary process 1000 provides operations for determining coordinates of the at least one target structure in the scout image, and performing an overlapping region optimization operation on the at least one target structure based on the coordinates of the at least one target structure. A position of each target structure in a scout image may be determined according to structure information of the target structure, and a position of the at least one target structure relative to an overlapping region may be determined based on the attribute of the at least one target structure, thus scanning parameters and bed positions for specific organs may be optimized, and effects on the scanning of unrelated organs may be avoided.

Figure 11:
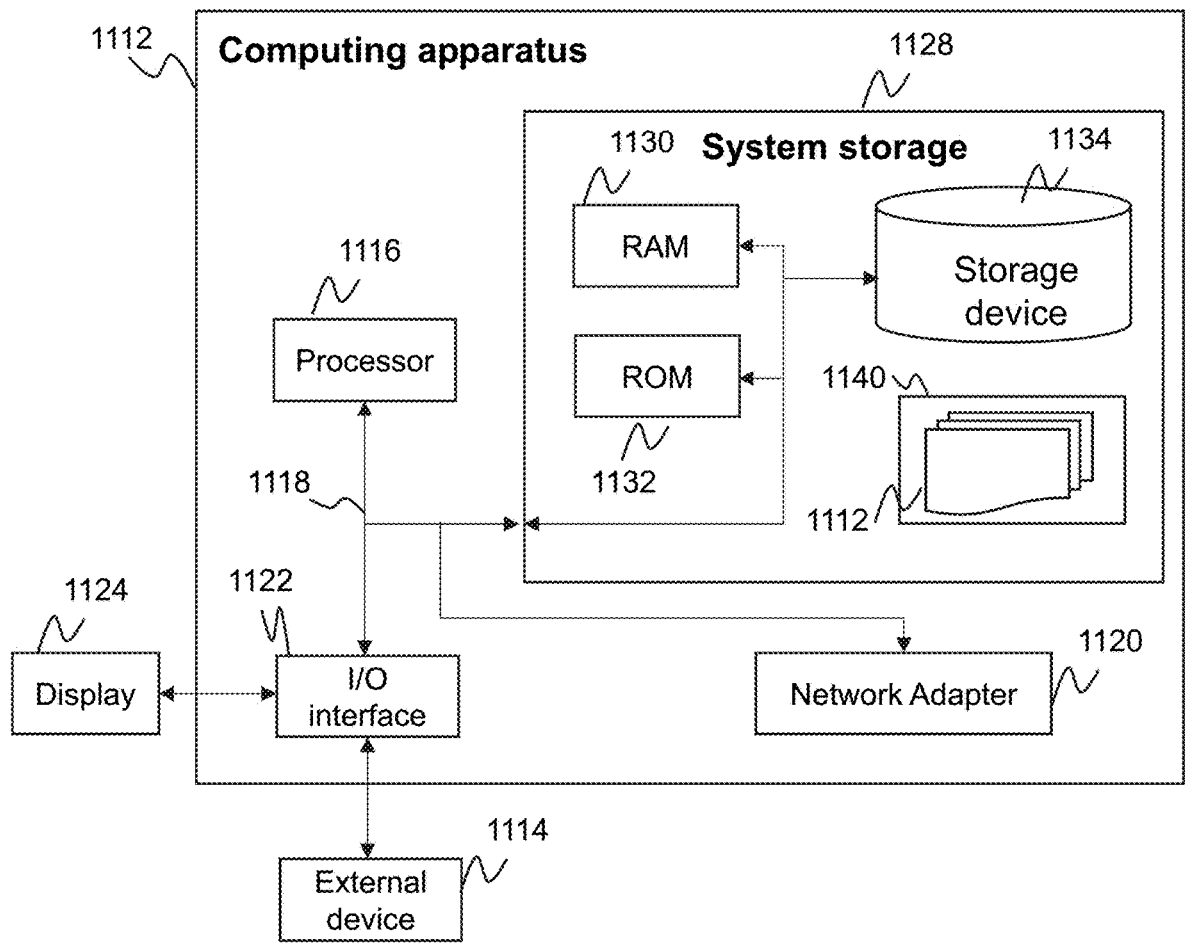
FIG. 11 is a schematic diagram of an exemplary computing apparatus according to some embodiments of the present disclosure.

FIG. 11 is a schematic diagram of an exemplary computing apparatus according to some embodiments of the present disclosure. The computing apparatus 1112 may facilitate the implementation of the processes or operations provided in the present disclosure. The computing apparatus 1112 illustrated in FIG. 11 is merely an example, but not intended to limit the scope of the present disclosure.

As shown in FIG. 11, the computing apparatus 1112 may be implemented by a computing apparatus of general purposes. The computing apparatus 1112 may include but are not limited to one or more processors 1116, a system memory 1128, and a bus 1118 that connects elements or components of the computing apparatus 1112, such as the system memory 1128, the one or more processors 1116, etc.

The bus 1118 may represent one or more of several types of bus structures, including a memory bus, a memory controller, peripheral bus, an accelerated graphics port, the one or more processors 1116, or a local bus using any of a variety of bus structures. For example, the bus structures may include but not limited to, an Industry Standard Architecture (ISA) bus, a Micro Channel Architecture (MAC) bus, an Enhanced ISA Bus, a Video Electronics Standards Association (VESA) local bus, a peripheral component interconnects (PCI) bus, etc.

The computing apparatus 1112 may include a variety of computer readable media. The computer readable media may be any available media including volatile or non-volatile media, removable or non-removable media, etc., that may be accessible by the computing apparatus 1112.

The system memory 1128 may include computer readable media in a form of volatile memory, for example, a random access memory (RAM) 1130 and/or a read-only memory (ROM) 1132. The computing apparatus 1112 may further include other removable/non-removable or volatile/non-volatile computer system storage media. Merely by ways of example, a storage device 1134 may be non-removable, non-volatile magnetic media (not shown in the figure, commonly referred to as a "hard disk drive") for reading and writing. Although not shown in FIG. 11, a disk drive for reading and writing to a removable non-volatile disk (such as a "floppy disk") and a removable non-volatile disk (such as a CD-ROM, a DVD-ROM, or other optical media) may be provided. In these cases, each drive may be coupled to the bus 1118 via one or more data medium ports. The system memory 1128 may include at least one program product having a set (e.g., at least one) of program modules configured to implement the functions provided in the above embodiments of the present disclosure.

A program/utility tool 1140 having a set (at least one) of program modules 1142, which may be stored, for example, in the memory 1128. The program modules 1142 may include but not limited to, an operating system, one or more applications, other program modules, or program data. Each or a combination of one or more of the above listed program modules may have a network environment implementation. The program module 1142 may perform the functions and/or methods provided in the described embodiments of the present disclosure.

The computing apparatus 1112 may also be in communication with one or more external devices 1114 (e.g., a keyboard, a pointing device, a display 1124, etc.), one or more devices that enable a user to interact with the computing apparatus 1112, and/or any devices (e.g., a network card, a modem, etc.) that enable the computing apparatus 1112 to communicate with one or more other computing apparatuses. The communication may be realized via an input/output (I/O) interface 1122. Also, the computing apparatus 1112 may also communicate with one or more networks (e.g., a local area network (LAN), a wide area network (WAN), and/or a public network, such as the Internet) through a network adapter 1120. As shown in the figure, the network adapter 1120 may communicate with other modules of computing apparatus 1112 via the bus 1118. It should be understood that, other hardware and/or software modules may be utilized in combination with the computing apparatus 1112, including but not limited to microcode, device drivers, redundant processing units, external disk drive arrays, RAID systems, Tape drives, or data backup storage systems.

The one or more processors 1116 may implement, by running a program stored in the system memory 1128, various functional applications and/or data processing, for example, a method of automated positioning of a subject for medical imaging or treatment provided in some embodiments of the present disclosure. According to a first aspect of the present disclosure, the method may include obtaining, by the computing apparatus 1112, a scout image of a subject. The method may also include determining, by the computing apparatus 1112, location information of at least one target structure of the subject based on the scout image. The method may further include determining, by the computing apparatus 1112, a protocol for performing a procedure regarding the at least one target structure according to the location information of the at least one target structure of the subject. According to a second aspect of the present disclosure, the method may include obtaining a scout image of a subject when the subject is positioned at a first position in an apparatus. The method may also include determining location information of a reference structure of the subject based on the scout image. The method may further include determining an offset between the first position of the subject relative to a characteristic point of the apparatus according to the location information of the reference structure. The method may further include moving the subject to a second position based on the offset. The method may still further include performing, using the apparatus, a procedure on a target structure of the subject located at the second position.

Those skilled in the art may understand that the one or more processors 1116 may also implement technical solutions of the exposure process control method provided by any embodiments of the present disclosure.

The present disclosure may further provide a computer readable storage medium storing computer programs. When the computer programs are executed by a processor, operations regarding automated positioning of a subject for a medical imaging or treatment provided in the present disclosure may be implemented. According to a first aspect of the present disclosure, the operations may include obtaining, by the computing apparatus 1112, a scout image of a subject. The operations may also include determining, by the computing apparatus 1112, location information of at least one target structure of the subject based on the scout image. The operations may further include determining, by the computing apparatus 1112, a protocol for performing a procedure regarding the at least one target structure according to the location information of the at least one target structure of the subject. According to a second aspect of the present disclosure, the operations may include obtaining a scout image of a subject when the subject is positioned at a first position in an apparatus. The operations may also include determining location information of a reference structure of the subject based on the scout image. The operations may further include determining an offset between the first position of the subject relative to a characteristic point of the apparatus according to the location information of the reference structure. The operations may further include moving the subject to a second position based on the offset. The operations may still further include performing, using the apparatus, a procedure on a target structure of the subject located at the second position.

It should be noted that the computer programs stored in the computer readable storage medium may not limited to the methods or operations provided above, other methods or operations related to the automated positioning of the subject may also be provided.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, microcode, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device storing a set of instructions; and
   at least one processor configured to communicate with the at least one storage device, wherein when executing the set of instructions, the at least one processor is directed to perform operations including:
      obtaining a scout image of a subject when the subject is positioned at a first position in an apparatus;
      determining location information of a reference structure of the subject based on the scout image;
      determining an offset between the first position of the subject relative to a characteristic point of the apparatus according to the location information of the reference structure;
      determining location information of a target structure of the subject based on the scout image;
      determining an auxiliary offset between the target structure and the characteristic point of the apparatus according to the location information of the target structure and an imaging-scan region;
      moving the subject to a second position based on the offset and the auxiliary offset; and
      performing, using the apparatus, a procedure relating to the target structure of the subject located at the second position.

2. The system of claim 1, wherein determining the offset between the first position of the subject relative to a characteristic point of the apparatus according to the location information of the reference structure includes:
   determining a coordinate of an edge point or a center point of the reference structure at the first position and a coordinate of the characteristic point of the apparatus; and
   determining the offset between the first position of the subject relative to a characteristic point of the apparatus based on the coordinate of the edge point or the center point of the reference structure at the first position and the coordinate of the characteristic point of the apparatus.

3. The system of claim 1, the apparatus including an imaging device, wherein the characteristic point of the apparatus includes an imaging center of the imaging device, and performing, using the apparatus, the procedure on the target structure of the subject located at the second position includes:
   directing the imaging device to scan the imaging-scan region including the target structure to obtain image data; and
   reconstructing an image of the target structure based on the image data.

4. The system of claim 1, the apparatus including a treatment device, wherein the characteristic point of the apparatus includes an isocenter of the treatment device, and performing, using the apparatus, the procedure on the target structure of the subject located at the second position includes:
   directing the treatment device to deliver a dose of a treatment medium to the target structure.

5. The system of claim 1, wherein obtaining the scout image of the subject positioned at the first position in the apparatus including:
   generating scanning instructions for scanning the subject or a portion of the subject when the subject is positioned at the first position in the apparatus;
   determining a pre-scan region based on the scanning instructions;
   obtaining pre-scan data of the pre-scan region by directing an imaging scanner to scan the pre-scan region;
   reconstructing one or more sub-images of the pre-scan region based on the pre-scan data; and
   generating the scout image based on the one or more sub-images.

6. The system of claim 1, wherein the target structure is different from the reference structure.

7. A system, comprising:
   at least one storage device storing a set of instructions; and
   at least one processor configured to communicate with the at least one storage device, wherein when executing the set of instructions, the at least one processor is directed to perform operations including:
      obtaining a scout image of a subject;
      determining location information of at least one target structure of the subject based on the scout image;
      determining a protocol for performing a procedure regarding the at least one target structure according to the location information of the at least one target structure of the subject, the protocol including a plurality of scanning regions and scanning parameters regarding the plurality of scanning regions;
      determining that at least one of the at least one target structure includes a dynamic structure;
      determining a coordinate of a center of the dynamic structure; and
      positioning the dynamic structure in a non-overlapping region in one of two adjacent scanning regions according to the coordinate of the center of the dynamic structure.

8. The system of claim 7, wherein the procedure includes imaging the at least one target structure of the subject or performing a treatment on the at least one target structure of the subject.

9. The system of claim 7, the operations further including:
   directing an imaging scanner to scan an imaging-scan region including the target structure according to the protocol to obtain image data; and reconstructing an image of the target structure based on the image data.

10. The system of claim 7, wherein obtaining the scout image of the subject includes:
generating scanning instructions for scanning the subject or a portion thereof;
determining a pre-scan region based on the scanning instructions;
obtaining pre-scan data of the pre-scan region by directing an imaging scanner to scan the pre-scan region;
reconstructing one or more sub-images of the pre-scan region based on the pre-scan data; and
generating the scout image based on the one or more sub-images.

11. The system of claim 7, wherein determining the location information of the at least one target structure of the subject based on the scout image includes: determining a coordinate of an edge point or a center point of the target structure in a length direction of the subject in the scout image.

12. The system of claim 7, wherein determining the protocol for performing the procedure regarding the at least one target structure according to the location information of the at least one target structure of the subject includes:
determining the plurality of scanning regions based on a coordinate of the at least one target structure.

13. The system of claim 7, wherein positioning the dynamic structure in the non-overlapping region in one of two adjacent scanning regions according to the coordinate of the center of the dynamic structure includes:
designating the coordinate of the center of the dynamic structure as a coordinate of the center of the one of the two scanning regions where the dynamic structure is located.

14. The system of claim 7, the operations further including:
determining that at least one of the at least one target structure includes a static structure;
determining coordinates of an upper edge and a lower edge of the static structure; and
positioning the static structure in an overlapping region of two adjacent scanning regions according to the coordinates of the upper edge and the lower edge of the static structure.

15. A method implemented on a computing apparatus having a processor and a computer-readable storage device, the method comprising:
obtaining a scout image of a subject when the subject is positioned at a first position in an apparatus;
determining location information of a reference structure of the subject based on the scout image;
determining an offset between the first position of the subject relative to a characteristic point of the apparatus according to the location information of the reference structure;
determining location information of a target structure of the subject based on the scout image;
determining an auxiliary offset between the target structure and the characteristic point of the apparatus according to the location information of the target structure and an imaging-scan region;
moving the subject to a second position based on the offset and the auxiliary offset; and
performing, using the apparatus, a procedure relating to the target structure of the subject located at the second position.

16. The method of claim 15, wherein determining the offset between the first position of the subject relative to a characteristic point of the apparatus according to the location information of the reference structure includes:
determining a coordinate of an edge point or a center point of the reference structure at the first position and a coordinate of the characteristic point of the apparatus; and
determining the offset between the first position of the subject relative to a characteristic point of the apparatus based on the coordinate of the edge point or the center point of the reference structure at the first position and the coordinate of the characteristic point of the apparatus.

* * * * *